US008436067B2

(12) United States Patent (10) Patent No.: US 8,436,067 B2
Thalacker et al. (45) Date of Patent: May 7, 2013

(54) INITIATOR SYSTEM WITH BIPHENYLENE DERIVATES, METHOD OF PRODUCTION AND USE THEREOF

(75) Inventors: Christoph Thalacker, Weilheim (DE); Bettina Hailand, Herrsching a Ammersee (DE); Karsten Dede, Landsberg (DE); Adrian S. Eckert, Herrsching (DE)

(73) Assignee: 3M Innovative Properties Company, Saint Paul, MN (US)

( * ) Notice: Subject to any disclaimer, the term of this patent is extended or adjusted under 35 U.S.C. 154(b) by 171 days.

(21) Appl. No.: 12/996,894

(22) PCT Filed: Jun. 10, 2009

(86) PCT No.: PCT/US2009/046850
§ 371 (c)(1),
(2), (4) Date: Dec. 8, 2010

(87) PCT Pub. No.: WO2009/152211
PCT Pub. Date: Dec. 17, 2009

(65) Prior Publication Data
US 2011/0124764 A1 May 26, 2011

(30) Foreign Application Priority Data

Jun. 10, 2008 (EP) .................. 08157903

(51) Int. Cl.
*A61K 6/083* (2006.01)
*C08B 37/00* (2006.01)
*C08F 2/50* (2006.01)
*H05B 6/68* (2006.01)
*B29C 71/04* (2006.01)
*C08G 61/04* (2006.01)

(52) U.S. Cl.
USPC ............ 522/30; 522/7; 522/6; 522/1; 522/71; 520/1

(58) Field of Classification Search .................. 522/30, 522/7, 6, 1, 71; 520/1
See application file for complete search history.

(56) References Cited

U.S. PATENT DOCUMENTS

| | | |
|---|---|---|
| 3,018,262 A | 1/1962 | Schroeder |
| 3,117,099 A | 1/1964 | Proops |
| 3,729,313 A | 4/1973 | Smith |
| 3,741,769 A | 6/1973 | Smith |
| 3,808,006 A | 4/1974 | Smith |
| 4,259,075 A | 3/1981 | Yamauchi |
| 4,298,738 A | 11/1981 | Lechtken |
| 4,324,744 A | 4/1982 | Lechtken |
| 4,356,296 A | 10/1982 | Griffith |
| 4,385,109 A | 5/1983 | Lechtken |
| 4,499,251 A | 2/1985 | Omura |
| 4,503,169 A | 3/1985 | Randklev |
| 4,537,940 A | 8/1985 | Omura |
| 4,539,382 A | 9/1985 | Omura |
| 4,588,756 A | 5/1986 | Bowen |
| 4,629,746 A | 12/1986 | Michl |
| 4,642,126 A | 2/1987 | Zador |
| 4,648,843 A | 3/1987 | Mitra |
| 4,652,274 A | 3/1987 | Boettcher |
| 4,665,217 A | 5/1987 | Reiners |
| 4,695,251 A | 9/1987 | Randklev |
| 4,710,523 A | 12/1987 | Lechtken |
| 4,735,632 A | 4/1988 | Oxman |
| 4,737,593 A | 4/1988 | Ellrich |
| 4,752,338 A | 6/1988 | Reiners |
| 4,767,798 A | 8/1988 | Gasser |
| 4,828,583 A | 5/1989 | Oxman |
| 4,835,193 A | 5/1989 | Hayase |
| 4,872,936 A | 10/1989 | Engelbrecht |
| 4,882,365 A | 11/1989 | Gasser |
| 4,889,792 A | 12/1989 | Palazzotto |
| 4,959,297 A | 9/1990 | Palazzotto |
| 5,026,902 A | 6/1991 | Fock |
| 5,076,844 A | 12/1991 | Fock |
| 5,130,347 A | 7/1992 | Mitra |
| 5,154,762 A | 10/1992 | Mitra |
| 5,332,429 A | 7/1994 | Mitra |
| 5,501,727 A | 3/1996 | Wang |
| 5,530,038 A | 6/1996 | Yamamoto |
| 5,545,676 A | 8/1996 | Palazzotto |
| 5,624,260 A | 4/1997 | Wilcox |

(Continued)

FOREIGN PATENT DOCUMENTS

| | | |
|---|---|---|
| CN | 1252138 | 5/2000 |
| EP | 173567 | 3/1986 |

(Continued)

OTHER PUBLICATIONS

Beringer, Diarylidonium Salts, IX, The Synthesis of Substituted Diphenyliodonium Salts, J. Am. Chem. Soc., vol. 81, pp. 342-351, (1959).
Din En ISO 4049, "Dentistry—Polymer-Based Filling, Restorative and Luting Meterials", Jan. 2001, pp. 1-29.
"Hydroxypropl Methacrylate (Stabilised)", Merck KGaA, Darmstadt, Germany, [online], retrieved from the internet on Jul. 14, 2010, <www.merck-chemicals.com/hydroproply-methacrylate/MDA_CHEM-800610/p_...>, pp. 1-3.
ISO 9917-1, "Dentistry—Water-Based Cements—Part 1: Powder/Liquid Acid-Base Cements", Nov. 1, 2003, pp. 1-22.
Moszner, Chemical Aspects of Self-Etching Enamel-Dentin Adhesives: A Systematic Review, Dental Materials, vol. 21, pp. 895-910, (2005).

(Continued)

*Primary Examiner* — Ling Choi
*Assistant Examiner* — Jessica E Whiteley
(74) *Attorney, Agent, or Firm* — Carlos M. Téllez; 3M Innovative Properties Company

(57) ABSTRACT

The invention relates to an initiator system comprising (a) an iodonium salt, (b) a light sensitizer and (c) an electron donor compound comprising a biphenylene structure, the biphenylene structure comprising at least one but not more than about 4 alkyl groups. The invention also relates to a hardenable composition comprising such an initiator system and the use thereof, as well as to a process for producing the substituted biphenylene compound.

19 Claims, No Drawings

U.S. PATENT DOCUMENTS

| | | |
|---|---|---|
| 5,684,060 A | 11/1997 | Konings |
| 5,730,764 A | 3/1998 | Williamson |
| 5,856,373 A | 1/1999 | Kaisaki |
| 5,865,803 A | 2/1999 | Major |
| 5,893,714 A | 4/1999 | Arnold |
| 5,918,772 A | 7/1999 | Keller |
| 5,944,419 A | 8/1999 | Streiff |
| 5,980,253 A | 11/1999 | Oxman |
| 5,998,495 A | 12/1999 | Oxman |
| 6,025,406 A | 2/2000 | Oxman |
| 6,030,606 A | 2/2000 | Holmes |
| 6,043,295 A | 3/2000 | Oxman |
| 6,187,833 B1 | 2/2001 | Oxman |
| 6,251,963 B1 | 6/2001 | Köhler |
| 6,306,926 B1 | 10/2001 | Bretscher |
| 6,387,981 B1 | 5/2002 | Zhang |
| 6,458,868 B1 | 10/2002 | Okada |
| 6,572,693 B1 | 6/2003 | Wu |
| 6,703,518 B1 | 3/2004 | Xu |
| 6,730,156 B1 | 5/2004 | Windisch |
| 6,765,036 B2 | 7/2004 | Dede |
| 6,790,877 B2 | 9/2004 | Nakatsuka |
| 6,899,948 B2 | 5/2005 | Zhang |
| 6,984,673 B2 | 1/2006 | Kawashima |
| 7,026,367 B2 | 4/2006 | Kalgutkar |
| 7,037,583 B2 | 5/2006 | Furman |
| 7,226,960 B2 | 6/2007 | Jia |
| 7,247,660 B2 | 7/2007 | Frances |
| 7,449,499 B2 | 11/2008 | Craig |
| 7,452,924 B2 | 11/2008 | Aasen |
| 2003/0018098 A1 | 1/2003 | Falsafi |
| 2003/0035899 A1 | 2/2003 | Klettke |
| 2003/0055123 A1 | 3/2003 | Kawashima |
| 2003/0166737 A1 | 9/2003 | Dede |
| 2003/0166740 A1 | 9/2003 | Mitra |
| 2003/0171505 A1 | 9/2003 | Bublewitz |
| 2003/0195273 A1 | 10/2003 | Mitra |
| 2004/0014009 A1 | 1/2004 | Jia |
| 2004/0235981 A1 | 11/2004 | Qian |
| 2005/0070627 A1 | 3/2005 | Falsafi |
| 2005/0113477 A1 | 5/2005 | Oxman |
| 2005/0175965 A1 | 8/2005 | Craig |
| 2005/0175966 A1 | 8/2005 | Falsafi |
| 2005/0176844 A1 | 8/2005 | Aasen |
| 2005/0252413 A1 | 11/2005 | Kangas |
| 2005/0252414 A1 | 11/2005 | Craig |
| 2005/0252415 A1 | 11/2005 | Budd |
| 2005/0256223 A1 | 11/2005 | Kolb |
| 2006/0084717 A1 | 4/2006 | Cohen |
| 2006/0144726 A1 | 7/2006 | Foust |
| 2006/0144733 A1 | 7/2006 | Wu |
| 2006/0187752 A1 | 8/2006 | Keller |
| 2007/0090079 A1 | 4/2007 | Kelller |
| 2007/0172789 A1 | 7/2007 | Muller |
| 2007/0243145 A1 | 10/2007 | Andre |
| 2007/0248927 A1 | 10/2007 | Luchterhandt |
| 2008/0193759 A1 | 8/2008 | Rieger |
| 2008/0293846 A1 | 11/2008 | Craig |
| 2008/0306168 A1 | 12/2008 | Craig |
| 2009/0047486 A1 | 2/2009 | Jones |
| 2009/0075239 A1 | 3/2009 | Abuelyaman |

FOREIGN PATENT DOCUMENTS

| | | |
|---|---|---|
| EP | 189540 | 8/1986 |
| EP | 201031 | 11/1986 |
| EP | 201778 | 11/1986 |
| EP | 238025 | 9/1987 |
| EP | 285369 | 10/1988 |
| EP | 320127 | 6/1989 |
| EP | 373384 | 6/1990 |
| EP | 412430 | 2/1991 |
| EP | 712622 | 5/1996 |
| EP | 728970 | 8/1996 |
| EP | 1051961 | 11/2000 |
| EP | 1340472 | 9/2003 |
| EP | 1465579 | 10/2004 |
| EP | 1586294 | 10/2005 |
| JP | 63273602 | 11/1988 |
| JP | 10147608 | 6/1998 |
| JP | 11322944 | 11/1999 |
| JP | 2001520758 | 10/2001 |
| WO | WO 9514716 | 6/1995 |
| WO | WO 9822521 | 5/1998 |
| WO | WO 9847046 | 10/1998 |
| WO | WO 9847047 | 10/1998 |
| WO | WO 9927892 | 6/1999 |
| WO | WO 0019966 | 4/2000 |
| WO | WO 0019967 | 4/2000 |
| WO | WO 0038619 | 7/2000 |
| WO | WO 0107444 | 2/2001 |
| WO | WO 0130305 | 5/2001 |
| WO | WO 0151540 | 7/2001 |
| WO | WO 0192271 | 12/2001 |
| WO | WO 03063804 | 8/2003 |
| WO | WO 2005051332 | 6/2005 |
| WO | WO 2006098882 | 9/2006 |
| WO | WO 2007079070 | 7/2007 |

OTHER PUBLICATIONS

Salz, Adhesion Performance of New Hydrolytically Stable One-Component Self-Etching Enamel/Dentin Adhesives, J. of Adhesive Dentistry, vol. 12, No. 1, pp. 7-11, (2010).
Intl Preliminary Report on Patentability and Written Opinion for PCT/US2006/049427, 5 pages.
Intl Preliminary Report on Patentability and Written Opinion for PCT/US2006/049463, 5 pages.
Intl Search Report for PCT/US2006/049463, 3 pages.
Intl Search Report for PCT/US2003/000522, 2 pages.
Written Opinion for PCT/US2003/000522, 5 pages.
Intl Preliminary Report and Written Opinion for PCT/US2006/049249, 5 pages.
Intl Search Report for PCT/US2006/049249, 3 pages.
Intl Preliminary Report on Patentability and Written Opinion for PCT/US2009/046850, 5 pages.
Intl Search Report for PCT/US2009/046850, 2 pages.
Constantine, Biphenylenes, Part XIV, Synthesis of 1- and 2-Phenyl-, 2,7-Dimethyl- and 2,3,6,7-Tetramethyl-Biphenylene, J. Chem. Soc. (C), vol. 19, pp. 1767-1769, (1966).
Wilcox, Jr., Preparation of Alykl-Substituted Biphenylenes by the Pyrolytic Extrusion of Nitrogen From Benzo[C]Cinnolines, J. Org. Chem. vol. 53, pp. 4333-4339, (1988).
Intl Search Report for PCT/US2006/049427, 3 pages.
Lee, Handbook of Epoxy Resins, 1967, McGraw-Hill Inc., New York (Table of Contents only).
Mann, Electrochemical Reactions in Nonaqueous Systems, 1970, Marcel Dekker, Inc., New York (Table of Contents only).
Weinberg, "Technique of Electroorganic Synthesis", Tehcniques of Chemistry, 1975, vol. V, Part II, John Wiley & Sons, New York (Table of Contents only).

INITIATOR SYSTEM WITH BIPHENYLENE DERIVATES, METHOD OF PRODUCTION AND USE THEREOF

CROSS REFERENCE TO RELATED APPLICATIONS

This application is a national stage filing under 35 U.S.C. 371 of PCT/US2009/46850, filed Jun. 10, 2009, which claims priority to European Patent Application No. 08157903.9, filed Jun. 10, 2008, the disclosure of which is incorporated by reference in its/their entirety herein.

FIELD OF THE INVENTION

In general, this invention relates to an initiator system for cationically hardenable resins. More specifically, this invention relates to photopolymerizable compositions that contain a cationically polymerizable resin and an initiator system that is activated upon exposure to actinic radiation. This invention also relates to methods of polymerizing such compositions using this initiator system in various applications including the dental and orthodontic area.

BACKGROUND ART

Epoxy-containing compounds are known to be curable using various cationic initiator systems.

E.g. Smith, U.S. Pat. No. 4,256,828, describes photopolymerizable compositions that contain epoxides, an organic compound with hydroxyl functionality, and a photosensitive aromatic sulfonium or iodonium salt of a halogen containing complex ion.

Hayase et al., U.S. Pat. No. 4,835,193, describe photopolymerizable epoxy resin compositions that comprise an epoxy resin and a heteropoly-acid aromatic sulfonium salt as the photocuring catalyst.

In WO 95/14716 Neckers et al. describe photohardenable compositions that comprise a cationically polymerizable compound, a xanthene or fluorone dye, a hydrogen donor, and an onium salt.

Palazzotto et al., U.S. Pat. No. 5,545,676, describe addition polymerization of free-radically polymerizable materials. The disclosed photoinitiator system comprises an aryliodonium salt, a sensitizer, and an electron donor having an oxidation potential less than or equal to that of p-dimethoxybenzene.

Oxman et al., U.S. Pat. No. 6,025,406, U.S. Pat. No. 6,043,295, U.S. Pat. No. 5,998,495 and U.S. Pat. No. 6,187,833 describe a ternary photoinitiator system for curing of epoxy resins.

Weinmann et al., U.S. Pat. No. 6,084,004, describe compositions that undergo cationic curing and comprise a diaryliodonium compound, an alpha-dicarbonyl compound, a compound containing epoxide and/or oxetane groups, and an aromatic amine.

Especially for visible light cationically curing compositions a ternary photoinitiator system consisting of a sensitizer (e.g. a 1,2-diketone like e.g. camphorquinone (CQ)), a so-called electron donor (e.g. polycyclic aromatic compounds like e.g. anthracene and/or derivatives thereof), and an acid generator (i.e. a latent Lewis and/or Broensted acid like e.g. an iodonium salt as proton generator) is used. Such systems are described e.g. in WO 03/059295 and WO 05/051332.

For visible light cationically curing dental compositions a ternary photoinitiator system consisting of a sensitizer (e.g. camphorquinone), an electron donor (e.g. anthracene) and an acid generator (e.g. diaryliodonium salt) overall show good performance.

SUMMARY

However, there is still a need for an improved curing system especially for cationically curing dental compositions. There is also a need for a system enabling the practitioner to provide a dental composition with good aesthetics.

In one embodiment the present invention features an initiator system (including a photoinitiator system) comprising:
(a) an iodonium salt;
(b) a visible light sensitizer and
(c) an electron donor compound comprising a biphenylene structure, the biphenylene structure comprising at least 1 but not more than about 4 alkyl (including C1 to C5) substituents directly attached onto the biphenylene structure.

A further embodiment of the invention is directed to hardenable composition comprising:
(b) the photoinitiator system described in the text of the invention.

The invention is also directed to a method for curing a polymerizable resin comprising the steps of:
providing a polymerizable composition as described in the text of the present invention and
exposing the polymerizable composition to a light source having a wavelength and intensity to which the photoinitiator system being present in the polymerizable composition is reactive.

Moreover, the invention features a method of using the hardenable composition as described in the text of the invention as a photopolymerizable adhesive, a curable ink imaging layer, a silverless imaging layer, an imaging layer on a projection plate, an imaging layer on a laser plate, or a dental material.

Yet a further embodiment of the invention is directed to a process for producing an electron donor compound comprising a biphenylene structure, wherein the process comprises the step of reacting a halogen-substituted benzene derivative with an organo Li reagent and subsequently with zinc chloride and copper chloride (preferably $CuCl_2$).

DEFINITIONS

The term "visible light" is used throughout this application to refer to light having a wavelength of about 400 to 1000 nanometers (nm).

A "dental composition" within the meaning of the invention is any composition which can be used in the dental field. In this respect the composition should be not detrimental to the patients' health and thus free of hazardous and toxic components being able to migrate out of the composition. Examples of dental compositions include permanent and temporary crown and bridge materials, artificial crowns, anterior or posterior filling materials, adhesives, mill blanks, lab materials and orthodontic devices.

A "monomer" within the meaning of the invention is any chemical substance which can be characterized by a chemical formula, bearing polymerizable groups (including (meth) acrylate groups) which can be polymerized to oligomers or polymers thereby increasing the molecular weight. The molecular weight of monomers can usually simply be calculated based on the chemical formula given.

A "hardenable compound" within the meaning of the invention is any compound which can be cured or solidified e.g. by heating to cause polymerization, chemical crosslinking, radiation-induced polymerization or crosslinking or using a redox initiator. A hardenable compound may contain only one, two, three or more polymerizable groups. Typical examples of polymerizable groups include epoxy groups and unsaturated carbon groups, such as a vinyl group being present i.a. in a (methyl)acrylate group.

A "resin" within the meaning of the invention contains all hardenable compounds (monomers, oligomers and/or polymers) being present in the hardenable composition. The resin may contain only one hardenable compound or a mixture of different hardenable compounds.

"Filler" within the meaning of the invention contains all fillers being present in the hardenable composition. Only one type of filler or a mixture of different fillers can be used.

"Dispersed within the resin" means that filler particles are present in the resin as discrete, unassociated (i.e. non-agglomerated and non-aggregated) particles.

A "nano-sized filler" within the meaning of the invention is a filler, the individual particles thereof have a size in the region of nanometers, e.g. an average particle diameter of less than about 200 nm. Useful examples are given in U.S. Pat. No. 6,899,948 and U.S. Pat. No. 6,572,693, the content of which especially with regard to nano-sized silica particles is herein incorporated by reference.

An "initiator or initiator system" within the meaning of the invention is a substance being able to start the curing process of a hardenable compound.

A "curing, hardening or setting reaction" within the meaning of the invention is used interchangeable and refers to a reaction wherein physical properties such as viscosity and hardness of a composition changes over the time due to a chemical reaction between the individual components.

A "derivative" within the meaning of the invention is a chemical compound showing a chemical structure closely related to the corresponding reference compound and containing all featured structural elements of the corresponding reference compound but having small modifications like bearing in addition comparably small additional chemical groups like e.g. $CH_3$, Br, Cl, or F or not bearing comparably small chemical groups like e.g. $CH_3$ in comparison to the corresponding reference compound. The following examples might illustrate this: tetramethyl bis-phenol A bearing four additional methyl groups with respect to the reference compound bis-phenol A, and bis-phenol F not bearing two additional methyl groups with respect to the reference compound bis-phenol A are derivatives of bis-phenol A within the meaning of this definition.

"Ambient conditions" mean the conditions which the inventive composition is usually subjected to during storage and handling. Ambient conditions may, for example, be a pressure of about 900 to about 1100 mbar, a temperature of about −10 to about 60° C. and a relative humidity of about 10 to about 100%. In the laboratory ambient conditions are adjusted to about 23° C. and about 1013 mbar. In the dental and orthodontic field ambient conditions are reasonably understood as a pressure of about 950 to about 1050 mbar, temperature of about 15 to about 40° C. and relative humidity of about 20 to about 80%.

As used herein, "a", "an", "the", "at least one" and "one or more" are used interchangeably. The terms "comprises" or "contains" and variations thereof do not have a limiting meaning where these terms appear in the description and claims. Also herein, the recitations of numerical ranges by endpoints include all numbers subsumed within that range (e.g., 1 to 5 includes 1, 1.5, 2, 2.75, 3, 3.80, 4, 5, etc.).

Unless otherwise indicated, all numbers expressing quantities of ingredients, measurement of properties such as contrast ratio and so forth used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings of the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviations found in their respective testing measurements.

DETAILED DESCRIPTION OF THE INVENTION

It has been found that biphenylene derivatives comprising a limited number of alkyl groups but typically no alkoxy groups are suitable electron donors especially for cationically curing compositions. These derivatives can be used as an alternative to polycyclic aromatic electron donors like e.g. anthracene and its derivatives like 2-Ethyl-9,10-dimethoxyanthracene (EDMO).

Moreover, it was found that compositions comprising the inventive photoinitiator system often show comparable, sometimes even improved properties compared to the corresponding compositions comprising anthracene derived electron donors instead of biphenylene derivatives.

Furthermore, it has been revealed that hardenable compositions containing the biphenylene derivatives of the present invention show improved properties compared to hardenable compositions containing either a non-substituted biphenylene compound or biphenylene compounds bearing a huge number of substituents.

One feature, which can be important for the dental practitioner is the colour of the cured or hardened composition. The colour can be evaluated e.g. by measuring the L*a*b* values, especially the b* value. A high b* value typically corresponds to a yellow appearance, which is often not desirable. It was found that dental compositions comprising the inventive initiator system have an acceptable b* value.

Another feature, which might contribute to the aesthetics of a dental composition, is the fluorescence. Whereas a slight fluorescence is sometimes desirable, a heavy fluorescence is often unwanted. It was found that dental compositions comprising the inventive initiator system have an acceptable fluorescence.

A further feature, which typically is desirable for innovative dental materials, is sufficient reactivity. A common method for determining the reactivity is the analysis of the depth of cure, which can be achieved. It was found that the inventive initiator system allows for a sufficient depth of cure, if added to polymerizable resins.

Thus, certain embodiments of the inventive compositions may provide a very useful combination of features like polymerization speed, polymerization depth, and shelf life.

The enhancement in the cure speed and cure depth which may be realized by this invention may allow a dentist to prepare and cure larger restorations at one time, thereby saving time and effort. The reduction in unwanted colour formation and improved colour stability can also make matching the restorative to various tooth shades easier and more accurate.

In certain embodiments the inventive composition fulfils at least one of the following features after hardening:
- Compressive strength (MPa): at least about 310 or at least about 320 or at least about 330, determined according to ISO 9917 using cubic specimen (dimensions 3 mm×3 mm×5 mm);
- Flexural strength (MPa): at least about 100 or at least about 110 or at least about 120 determined according to ISO 4049;
- E-modulus (GPa): at least about 8 or at least about 9 or at least about 10 determined according to ISO 4049;
- Bonded disk shrinkage-strain (vol.-%): less or equal than about 1.1 or less or equal than about 1.0 or less or equal than about 0.9 determined according to the Watts protocol;
- Depth of cure (measured values of depth of cure in a metal mould according to ISO 4049), at least about 2.10 mm;
- Depth of cure (measured values of depth of cure in a Delrin mould according to ISO 4049), at least about 3.50 mm;
- Color of the cured composition (measured values of $L^*$, $a^*$, and $b^*$), with $b^*$ having a value of less or equal than about 14.0 or less or equal than about 12.0 or less or equal than about 10.0; and/or
- Lack of intense fluorescence (determined as described in the example section) e.g., in a wavelength range of about 370 nm to about 650 nm, the composition being irradiated with monochromatic radiation of about 355 nm wavelength at 23° C. The composition typically does show not more than about 70% or not more than about 50% or not more than about 30% or not more than about 20% fluorescence compared to a composition containing EDMO instead of the inventive diarylalkylamine compound.

For certain embodiments (e.g. dental composite materials), a combination of the following parameters can be preferred: colour (especially $b^*$ value; e.g. less than about 12), lack of intense fluorescence of the cured composition (e.g. less than about 20%, if measured as described above) and depth of cure (e.g. at least about 2.1, if measured in a metal mold).

The first component in the photoinitiator system is an iodonium salt, e.g., a diaryliodonium salt. The iodonium salt should be soluble in the composition and preferably is shelf-stable, meaning it does not spontaneously promote polymerization when dissolved therein in the presence of the visible light sensitizer and the electron donor compound. Accordingly, selection of a particular iodonium salt may depend to some extent upon the particular resin, visible light sensitizer and electron donor that are chosen. Suitable iodonium salts are described in U.S. Pat. Nos. 3,729,313, 3,741,769, 3,808,006, 4,250,053 and 4,394,403. The iodonium salt can be a simple salt, containing an anion such as $Cl^-$, $Br^-$, $I^-$ or $C_2H_5SO_3^-$; or a metal complex salt containing an antimonate, arsenate, phosphate or borate such as $SbF_5OH^-$ or $AsF_6^-$. Combinations of iodonium salts can be used if desired.

Examples of useful aromatic iodonium complex salt photoinitiators include: diphenyliodonium tetrafluoroborate; di(4-methylphenyl)iodonium tetrafluoroborate; phenyl-4-methylphenyliodonium tetrafluoroborate; di(4-heptylphenyl)iodonium tetrafluoroborate; di(3-nitrophenyl)iodonium hexafluorophosphate; di(4-chlorophenyl)iodonium hexafluorophosphate; di(naphthyl)iodonium tetrafluoroborate; di(4-trifluoromethylphenyl)iodonium tetrafluoroborate; diphenyliodonium hexafluorophosphate; di(4-methylphenyl)iodonium hexafluorophosphate; diphenyliodonium hexafluoroarsenate; di(4-phenoxyphenyl)iodonium tetrafluoroborate; phenyl-2-thienyliodonium hexafluorophosphate; 3,5-dimethylpyrazolyl-4-phenyliodonium hexafluorophosphate; diphenyliodonium hexafluoroantimonate; 2,2'-diphenyliodonium tetrafluoroborate; di(2,4-dichlorophenyl)iodonium hexafluorophosphate; di(4-bromophenyl)iodonium hexafluorophosphate; di(4-methoxyphenyl)iodonium hexafluorophosphate; di(3-carboxyphenyl)iodonium hexafluorophosphate; di(3-methoxycarbonylphenyl)iodonium hexafluorophosphate; di(3-methoxysulfonylphenyl)iodonium hexafluorophosphate; di(4-acetamidophenyl)iodonium hexafluorophosphate; di(2-benzothienyl)iodonium hexafluorophosphate; and diphenyliodonium hexafluoroantimonate.

Of the aromatic iodonium complex salts which are suitable for use in the compositions of the invention diaryliodonium hexafluorophosphate, diaryliodonium hexafluoroantimonate, 4-octyloxyphenyl phenyliodonium hexafluoroantimonate, 4-(2-hydroxytetradecyloxyphenyl)phenyliodonium hexafluoroantimonate, and 4-(1-methylethyl)phenyl 4-methylphenyliodonium tetrakis(pentafluorophenyl)borate are among the preferred salts. These salts are preferred because, in general, they promote faster reaction, and are more soluble in inert organic solvents than are other aromatic iodonium salts of complex ions.

The aromatic iodonium complex salts may be prepared by metathesis of corresponding aromatic iodonium simple salts (such as, for example, diphenyliodonium bisulfate). Thus, for example, the complex salt diphenyliodonium tetrafluoroborate can be prepared by the addition at 60° C. of an aqueous solution containing 29.2 g silver fluoroborate, 2 g fluoroboric acid, and 0.5 g phosphorous acid in about 30 ml of water to a solution of 44 g (139 millimoles) of diphenyliodonium chloride. The silver halide that precipitates is filtered off and the filtrate concentrated to yield diphenyliodonium fluoroborate which may be purified by recrystallization.

The aromatic iodonium simple salts may be prepared by various methods including (1) coupling of two aromatic compounds with iodyl sulfate in sulfuric acid, (2) coupling of two aromatic compounds with an iodate in acetic acid-acetic anhydride-sulfuric acid, (3) coupling of two aromatic compounds with an iodine acetate in the presence of an acid, and (4) condensation of an iodoso compound, an iodoso diacetate, or an iodoxy compound with another aromatic compound in the presence of an acid. Diphenyliodonium bisulfate is prepared by method (3), for example, by the addition over a period of eight hours at below 5° C. of a mixture of 35 ml of conc. sulfuric acid and 50 ml of acetic anhydride to a well-stirred mixture of 55.5 ml of benzene, 50 ml of acetic anhydride, and 53.5 g of potassium iodate. The mixture is stirred for an additional four hours at 0°-5° C. and at room temperature (about 25° C.) for 48 hours and treated with 300 ml of diethyl ether. On concentration, crude diphenyliodonium bisulfate precipitates and may be purified by recrystallization if desired.

The second component in the photoinitiator system is a light sensitizer, including visible sensitizers. The light sensitizer should be partly or fully soluble in the photopolymerizable composition, free of functionalities that would substantially interfere with the cationic polymerization process, and capable of light absorption somewhere within the range of wavelengths between about 400 and about 1000 nanometers (nm). Preferred visible light sensitizers contain one or more carbonyl functional groups.

Suitable visible light sensitizers may include compounds in the following categories: ketones, coumarin dyes (e.g., ketocoumarins), xanthene dyes, fluorone dyes, fluorescein dyes, aminoketone dyes, and p-substituted aminostyryl ketone compounds. Ketones (e.g., monoketones or alpha-diketones), coumarin dyes (e.g., ketocoumarins), xanthene dyes, fluorone dyes, and fluorescein dyes are particularly preferred visible light sensitizers for use in the invention. For applications requiring deep cure (e.g., cure of highly-filled composites), it is preferred to employ sensitizers having an extinction coefficient below about 1000 lmole$^{-1}$cm$^{-1}$, more preferably about or below 100 lmole$^{-1}$cm$^{-1}$, at the desired wavelength of irradiation for photopolymerization. The alpha-diketones are an example of a class of visible light sensitizers having this property, and are particularly preferred for dental applications.

By way of example, a preferred class of ketone visible light sensitizers has the formula:

where X is CO or CR$^1$R$^2$ where R$^1$ and R$^2$ can be the same or different, and can be hydrogen, alkyl, alkaryl or aralkyl, b is zero, and A and B can be the same or different and can be substituted (having one or more non-interfering substituents) or unsubstituted aryl, alkyl, alkaryl, or aralkyl groups, or together A and B can form a cyclic structure which can be a substituted or unsubstituted cycloaliphatic, aromatic, heteroaromatic or fused aromatic ring.

Suitable ketones of the above formula include monoketones (b=0) such as 2,2-, 4,4- or 2,4-dihydroxybenzophenone, di-2-pyridyl ketone, di-2-furanyl ketone, di-2-thiophenyl ketone, benzoin, fluorenone, chalcone, Michler's ketone, 2-fluoro-9-fluorenone, 2-chlorothioxanthone, acetophenone, benzophenone, 1- or 2-acetonaphthone, 9-acetylanthracene, 2-, 3- or 9-acetylphenanthrene, 4-acetylbiphenyl, propiophenone, n-butyrophenone, valerophenone, 2-, 3- or 4-acetylpyridine, 3-acetylcoumarin and the like. Suitable diketones include aralkyldiketones such as anthraquinone, phenanthrenequinone, o-, m- and p-diacetylbenzene, 1,3-, 1,4-, 1,5-, 1,6-, 1,7- and 1,8-diacetylnaphthalene, 1,5-, 1,8- and 9,10-diacetylanthracene, and the like. Suitable 1-diketones (b=1 and x=CO) include 2,3-butanedione, 2,3-pentanedione, 2,3-hexanedione, 3,4-hexanedione, 2,3-heptanedione, 3,4-heptanedione, 2,3-octanedione, 4,5-octanedione, benzil, 2,2'-3'- and 4,4'-dihydroxylbenzil, furil, di-3,3'-indolylethanedione, 2,3-bornanedione (camphorquinone), biacetyl, 1,2-cyclohexanedione, 1,2-naphthaquinone, acenaphthaquinone, 1-phenyl-1,2-propanedione, and the like.

Examples of particularly preferred visible light sensitizers include the alpha-diketones: camphorquinone; glyoxal; biacetyl; 3,3,6,6-tetramethylcyclohexanedione; 3,3,7,7-tetramethyl-1,2-cycloheptanedione; 3,3,8,8-tetramethyl-1,2-cyclooctanedione; 3,3,18,18-tetramethyl-1,2-cyclooctadecanedione; dipivaloyl; benzil; furil; hydroxybenzil; 2,3-butanedione; 2,3-pentanedione; 2,3-hexanedione; 3,4-hexanedione; 2,3-heptanedione; 3,4-heptanedione; 2,3-octanedione; 4,5-octanedione; 1,2-cyclohexanedione; and 1-phenyl-1,2-propanedione. Of these, camphorquinone is the most preferred visible light sensitizer.

Examples of preferred fluorone dyes include, but are not limited to, fluorescein, 4'5'-dibromofluorescein, erythrosin B, ethyl eosin, eosin Y, and erythrosin, yellowish blend.

The third component in the photoinitiator system is an electron donor compound.

A wide variety of electron donor compounds can be employed in the practice of the invention, and generally are capable of increasing the speed of polymerization and/or the depth of polymerization of a composition according to the invention when exposed to visible light of the desired wavelength, as compared to the same composition but excluding the electron donor compound.

The electron donor compound according to the invention comprises a biphenylene structure, which comprises alkyl groups but typically no alkoxy groups.

In a preferred embodiment the alkyl groups pending on the biphenylene ring structure are arranged symmetrically.

The alkyl substituents are preferably at the positions 2, 3, 6, and 7. In a further embodiment there are not more than 2 substituents at the positions 2 and 6 or 2 and 7. Preferably, the alkyl substituents are independently selected from methyl groups or tert-butyl groups. The biphenylene structure typically does not comprise alkoxy groups like e.g. methoxy groups, being directly attached onto the biphenylene structure.

Preferred electron donor compounds for use in the invention possess one or more (and more preferably several if not all) of the following properties:
(a) they are soluble in a polymerizable or hardenable composition;
(b) they do not absorb a significant amount of light at the wavelength of the light used to photopolymerize the composition, typically the wavelength at which the visible light sensitizer exhibits maximum absorption, by which it is meant that the electron donor compound does not detrimentally affect the performance of the visible light sensitizer;
(c) they have an oxidation potential ($E_{ox}$) greater than 0 but less than that of 1,4-dimethoxybenzene when measured versus a saturated calomel electrode (SCE); the oxidation potential is typically less than about 1.35 volts when measured using a saturated calomel electrode;
(d) they yield a photoinitiator system that has a photoinduced potential less than that of 3-dimethylaminobenzoic acid in a standard solution of $2.9 \times 10^{-5}$ moles/g diphenyl iodonium hexafluoroantimonate and $1.5 \times 10^{-5}$ moles/g camphorquinone in 2-butanone;
(e) they impart not more than a minimal amount of objectionable colour to the polymerized resin;
(f) they impart not more than a minimal amount of objectionable fluorescence to the polymerized resin;
(g) they can be used in a lower effective concentration than other polymerization aids. Other factors that may influence the selection of the electron donor compound for a particular composition include the cationically polymerizable resin, the iodonium salt, and the visible light sensitizer that have been chosen, as well as the shelf stability of the cationically polymerizable composition;
(h) they have a $pk_b$ value greater than about 8.

More specifically, electron donor compounds comprising the structure shown below may be employed.

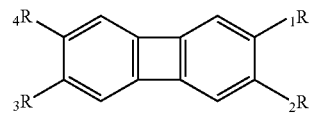

wherein each of $R_1$ to $R_4$ is independently selected from H, or alkyl groups, wherein the R-group substituents may also cooperate to form a cycloalkyl ring. Preferred R-group substituents include methyl, ethyl, iso-propy, n-propyl, and tert-butyl groups, with the methyl and tert-butyl groups being most preferred.

More specifically, according to a preferred embodiment the electron donor compound of the invention can be characterized by at least one of the following features:

a. The biphenylene compound bears at least one, two or three but not more than about four alkyl (e.g. C1 to C4) groups.
b. The substituted biphenylene compound is symmetric (reflection and/or rotation).
c. The biphenylene compound does not contain alkoxy groups directly attached onto the biphenylene structure.
d. The biphenylene compound has a molecular weight in the range of about 180 to about 380.

The combination of features a, c and d or b, c and d can be preferred.

Specific examples of biphenylene compounds which can be used have the following structures:

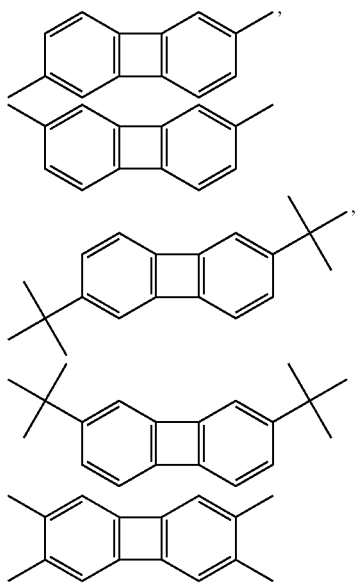

and derivatives and combinations thereof.

Another aspect of the invention is directed to a process of producing biphenylene derivatives. This process involves the steps of reacting a halogen-substituted benzene derivative with an organo Li reagent and subsequently with zinc chloride and copper chloride (preferably CuCl$_2$).

More specifically, the reaction can be described as follows:
Halogen metal exchange reaction of a bis halogen-substituted benzene derivative with an organo Li reagent.
Metathesis reaction using anhydrous zinc chloride.
C—C coupling reaction using anhydrous copper dichloride.

The reaction is typically carried out in anhydrous solvents inert to the reaction conditions. Solvents which can be used include THF, diethyl ether and hexane Moreover, the reaction is typically carried out at a low temperature (e.g. below about −40° C.) under anhydrous conditions (e.g. protective atmosphere of dry nitrogen or argon).

Organo Li reagents which can be used include n-Butyl-Lithium (n-BuLi) and Methyl-Lithium.

The halogen of the halogen-substituted benzene derivatives include F, Cl, Br and I, with Br and Cl being preferred.

A typical workup procedure may include the following steps:
Addition of diethylether to the reaction mixture.
Extraction of the mixture with water (preferably several times, e.g. 2, 3 or 4 times).
Optionally drying the diethylether fraction over a suitable drying agent (e.g. anhydrous sodium sulphate).
Removing the diethylether
Optionally treating the remaining product with n-hexane.
Alternatively or in addition, the product can be isolated by liquid chromatography, followed by fractionated crystallization if desired.

The reaction can be carried out as a one-pot synthesis, i.e. without isolating the intermediate products.

Depending on the stoichiometry of the reagents and the reaction conditions chosen (e.g. temperature and time) and the work-up procedure applied the overall yield of the final product can be optimized.

The cationically polymerizable resin may be selected from epoxy, oxetane, vinyl ether and spiro-orthocarbonate resins, and combinations thereof. Preferably, the cationically polymerizable resin comprises an epoxy resin, especially a silicon-containing epoxy resin, or a blend of a silicon-containing epoxy resin and an epoxy resin that does not contain silicon.

Advantageously, the photopolymerizable compositions of the invention are sensitive throughout the visible light region and polymerize without appreciable application of heat. Photopolymerization of the compositions takes place upon exposure of the compositions to a source of actinic radiation having a wavelength within this spectral region.

The cationically polymerizable resins useful in the compositions of the invention include, for example, epoxy (including silicon-containing epoxy), oxetane, spiro-orthocarbonate, and, vinyl ether resins, as well as combinations thereof.

Useful epoxy resins are organic compounds having an oxirane ring, i.e., a group of the formula

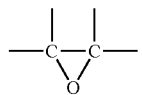

which is polymerizable by ring opening. Such materials, broadly called epoxides, include monomeric epoxy compounds and epoxides of the polymeric type and can be aliphatic, cycloaliphatic, aromatic or heterocyclic. These materials generally have, on the average, at least 1 polymerizable epoxy group per molecule, preferably at least about 1.5, and more preferably at least about 2 polymerizable epoxy groups per molecule. The polymeric epoxides include linear polymers having terminal epoxy groups (e.g., a diglycidyl ether of a polyoxyalkylene glycol), polymers having skeletal oxirane units (e.g., polybutadiene polyepoxide), and polymers having pendent epoxy groups (e.g., a glycidyl methacrylate polymer or copolymer). The epoxides may be pure compounds or may be mixtures of compounds containing one, two, or more epoxy groups per molecule. The "average" number of epoxy groups per molecule is determined by dividing the total number of epoxy groups in the epoxy resin by the total number of epoxy-containing molecules present.

These epoxy resins may vary from low molecular weight monomeric materials to high molecular weight polymers and may vary greatly in the nature of their backbone and substituent groups. For example, the backbone may be of any type and substituent groups thereon can be any group that does not substantially interfere with cationic polymerization at room temperature. Illustrative of permissible substituent groups are halogens, ester groups, ethers, sulfonate groups, siloxane groups, nitro groups, phosphate groups, and the like. The molecular weight of the epoxy resin may vary from about 58 to about 100,000 or more.

Particularly preferred epoxy resins include those which contain cyclohexene oxide groups such as epoxycyclohexanecarboxylates, typified by 3,4-epoxycyclohexylmethyl-3,4-epoxycyclohexanecarboxylate, 3,4-epoxy-2-methylcyclohexylmethyl-3,4-epoxy-2-methylcyclo-hexane carboxylate, and bis(3,4-epoxy-6-methylcyclohexylmethyl)adipate. For a more detailed list of useful epoxides of this nature, reference is made to U.S. Pat. Nos. 3,117,099 and 6,245,828. Other epoxy resins that are useful in the compositions of this invention include glycidyl ether monomers of the formula

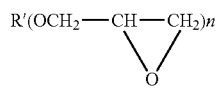

where R' is alkyl or aryl, and n is an integer of 1 to 6. Examples are glycidyl ethers of polyhydric phenols obtained by reacting a polyhydric phenol with an excess of chlorohydrin such as epichlorohydrin (e.g., the diglycidyl ether of 2,2-bis-(2,3-epoxypropoxyphenol)propane). Further examples of epoxides of this type are described in U.S. Pat. No. 3,018,262.

There is a host of commercially available epoxy resins that can be used in this invention. In particular, epoxides that are readily available include octadecylene oxide, epichlorohydrin, styrene oxide, vinyl cyclohexene oxide, glycidol, glycidylmethacrylate, diglycidyl ether of Bisphenol A (e.g., those available under the trade designations "Epon 828", "Epon 825", "Epon 1004" and "Epon 1010" from Shell Chemical Co., "DER-331", "DER-332", and "DER-334", from Dow Chemical Co.), vinylcyclohexene dioxide (e.g., "ERL-4206" from Union Carbide Corp.), 3,4-epoxycyclohexylmethyl-3,4-epoxycyclohexene carboxylate (e.g., "ERL-4221" or "CYRACURE UVR 6110" or UVR 6105" from Union Carbide Corp.), 3,4-epoxy-6-methylcyclohexylmethyl-3,4-epoxy-6-methyl-cyclohexene carboxylate (e.g., "ERL-4201" from Union Carbide Corp.), bis(3,4-epoxy-6-methylcyclohexylmethyl)adipate (e.g., "ERL-4289" from Union Carbide Corp.), bis(2,3-epoxycyclopentyl)ether (e.g., "ERL-0400" from Union Carbide Corp.), aliphatic epoxy modified from polypropylene glycol (e.g., "ERL-4050" and "ERL-4052" from Union Carbide Corp.), dipentene dioxide (e.g., "ERL-4269" from Union Carbide Corp.), epoxidized polybutadiene (e.g., "Oxiron 2001" from FMC Corp.), silicone resin containing epoxy functionality, flame retardant epoxy resins (e.g., "DER-580", a brominated bisphenol type epoxy resin available from Dow Chemical Co.), 1,4-butanediol diglycidyl ether of phenolformaldehyde novolak (e.g., "DEN-431" and "DEN-438" from Dow Chemical Co.), and resorcinol diglycidyl ether (e.g., "Kopoxite" from Koppers Company, Inc.), bis(3,4-epoxycyclohexyl)adipate (e.g., "ERL-4299" or "UVR-6128", from Union Carbide Corp.), 2-(3,4-epoxycyclohexyl-5,5-spiro-3,4-epoxy)cyclohexanemeta-dioxane (e.g., "ERL-4234" from Union Carbide Corp.), vinylcyclohexene monoxide 1,2-epoxyhexadecane (e.g., "UVR-6216" from Union Carbide Corp.), alkyl glycidyl ethers such as alkyl $C_8$-$C_{10}$ glycidyl ether (e.g., "HELOXY Modifier 7" from Shell Chemical Co.), alkyl $C_{12}$-$C_{14}$ glycidyl ether (e.g., "HELOXY Modifier 8" from Shell Chemical Co.), butyl glycidyl ether (e.g., "HELOXY Modifier 61" from Shell Chemical Co.), cresyl glycidyl ether (e.g., "HELOXY Modifier 62" from Shell Chemical Co.), p-tert-butylphenyl glycidyl ether (e.g., "HELOXY Modifier 65" from Shell Chemical Co.), polyfunctional glycidyl ethers such as diglycidyl ether of 1,4-butanediol (e.g., "HELOXY Modifier 67" from Shell Chemical Co.), diglycidyl ether of neopentyl glycol (e.g., "HELOXY Modifier 68" from Shell Chemical Co.), diglycidyl ether of cyclohexanedimethanol (e.g., "HELOXY Modifier 107" from Shell Chemical Co.), trimethylol ethane triglycidyl ether (e.g., "HELOXY Modifier 44" from Shell Chemical Co.), trimethylol propane triglycidyl ether (e.g., "HELOXY Modifier 48" from Shell Chemical Co.), polyglycidyl ether of an aliphatic polyol (e.g., "HELOXY Modifier 84" from Shell Chemical Co.), polyglycol diepoxide (e.g., "HELOXY Modifier 32" from Shell Chemical Co.), bisphenol F epoxides (e.g., "EPN-1138" or "GY-281" from Ciba-Geigy Corp.), 9,9-bis[4-(2,3-epoxypropoxy)-phenyl]fluorenone (e.g., "Epon 1079" from Shell Chemical Co.).

Still other useful epoxy resins contain copolymers of acrylic acid esters or glycidol such as glycidylacrylate and glycidylmethacrylate with one or more copolymerizable vinyl compounds. Examples of such copolymers are 1:1 styrene-glycidylmethacrylate, 1:1 methylmethacrylate-glycidylacrylate and a 62.5:24:13.5 methylmethacrylate-ethyl acrylate-glycidylmethacrylate.

Other useful epoxy resins include epichlorohydrins, alkylene oxides, e.g., propylene oxide, styrene oxide; alkenyl oxides, e.g., butadiene oxide; and glycidyl esters, e.g., ethyl glycidate.

Particularly preferred epoxides are those that contain silicon, useful examples of which are described in International Patent Publication No. WO 01/51540, such as: 7-Oxabicyclo[4.1.0]heptane; 3,3',3'",3""-[(2,4,6,8-tetramethylcyclotetrasiloxan-2,4,6,8-tetrayl)tetra-2,1-ethandiyl]tetrakis-; 7-Oxabicyclo[4.1.0]heptan, 3,3',3",3'",3""-[(2,4,6,8,10-pentamethylcyclo-pentasiloxan-2,4,6,8,10-pentayl)penta-2,1-ethandiyl]pentakis-, Silane; methylbis[2-(7-oxabicyclo[4.1.0]hept-3-yl)ethyl]phenyl-; Silane, dimethylbis[2-(7-oxabicyclo[4.1.0]hept-3-yl)methyl]-; Silane, dimethyl[2-(7-oxabicyclo[4.1.0]hept-3-yl)methyl][2-(7-oxabicyclo[4.1.0]hept-3-yl)ethyl]-; Silane, 1,4-phenylenbis[dimethyl[2-(7-oxabicyclo[4.1.0]hept-3-yl)ethyl]]-; Silane 1,2-ethylenbis[dimethyl[2-(7-oxabicyclo[4.1.0]hept-3-yl)ethyl]]-; Silane, dimethylbis[2-(7-oxabicyclo[4.1.0]hept-3-yl)ethyl]-; 1,3-Bis[2-(3,4-epoxycyclohexyl)ethyl]-1,1,3,3-tetramethyldisiloxane; Silane, 2,5-bicyclo[2.2.1.]heptylenbis[dimethyl[2-(7-oxabicyclo[4.1.0]hept-3-yl)ethyl]]-; Silane, 1,6-hexylenbis[dimethyl[2-(7-oxabicyclo[4.1.0]hept-3-yl)ethyl]]-; Silane, 1,1',1"-(1,2,4-cyclohexylentris(dimethyl[2-(7-oxabicyclo[4.1.0]hept-3-yl)ethyl]))-; Trisiloxane, 3-[[dimethyl[2-(7-oxabicyclo[4.1.0]hept-3-yl)ethyl]silyl]oxy]-1,1,5,5-tetramethyl-1,5-bis[2-(7-oxabicyclo[4.1.0]hept-3-yl)ethyl]-3-phenyl-; Disiloxane, 1,1',1"-(1,2,4-cyclohexanetriyltri-2,1-ethanediyl)tris[1,1,3,3-tetramethyl-3-[2-(7-oxabicyclo[4.1.0]hept-3-yl)ethyl]]-; Trisiloxane, 3,3-bis[[dimethyl[2-(7-oxabicyclo[4.1.0]hept-3-yl)ethyl]silyl]oxy]-1,1,5,5-tetramethyl-1,5-bis[2-(7-oxabicyclo[4.1.0]hept-3-yl)ethyl]-; Trisiloxane, 3-[[dimethyl[2-(7-oxabicyclo[4.1.0]hept-3-yl)ethyl]silyl]oxy]-1,1,3,5,5-pentamethyl-1,5-bis[2-(7-oxabicyclo[4.1.0]hept-3-yl)ethyl]-; 1,3,5,7-tetrakis(2,1-ethandiyl-3,4-epoxycyclohexyl)-1,3,5,7-tetramethylcyclo-tetrasiloxane and 1,3,5,7,9-pentakis(2,1-ethandiyl-3,4-epoxycyclohexyl)-1,3,5,7,9-pentamethylcyclopentasiloxane.

The cationically polymerizable resin may also be provided by a vinyl ether resin. Examples of vinyl ether resins that may be used include, but are not limited to, tri(ethylene glycol) divinyl ether (TEGDVE), glycidyl vinyl ether (GVE), butanediolvinyl ether (BDVE), di(ethylene glycol) divinyl ether (DEGDVE), 1,4-cyclohexanedimethdiol divinyl ether (CHDMDVE), 4-(isopropenyloxymethyl)-1,3-dioxolan-2-one (POMDO), 2-chloroethyl vinyl ether (CEVE), 2-ethylhexyl vinyl ether (EHVE), ethyl vinyl ether (EVE), n-propyl vinyl ether (NPVE), isopropyl vinyl ether (IPVE), n-butyl vinyl ether (NBVE), isobutyl vinyl ether (IBVE), octadecyl vinyl ether (ODVE), cyclohexyl vinyl ether (CVE), butanediol divinyl ether (BDDVE), hydroxybutyl vinyl ether (HBVE), cyclohexanedimethanol monovinyl ether (CHMVE), tert-butyl vinyl ether (TBVE), tert-amyl vinyl ether (TAVE), dodecyl vinyl ether (DDVE), ethylene glycol divinyl ether (EGDVE), ethylene glycol monovinyl ether (EGMVE), hexanediol divinyl ether (HDDVE), hexanediol monovinyl ether (HDMVE), diethylene glycol monovinyl ether (MVE-2), triethyleneglycol methyl vinyl ether (MTGVE), tetraethylene glycol divinyl ether (DVE-4), trimethylolpropane trivinyl ether (TMPTVE), aminopropyl vinyl ether (APVE), polytetrahydrofuran divinyl ether (PTHFDVE), n-butyl vinyl ether (n-BVE), 4-hydroxybutyl vinyl ether (HBVE), ethylene glycol butyl vinyl ether (EGBVE), 2-diethylamino ethyl vinyl ether (DEAEVE), dipropylene glycol divinyl ether (DPGDVE), a vinyl ether terminated aromatic ester monomer (e.g., hydroxybutyl vinyl ether isophthalate which can be purchased from Allied-Signal Inc., Engineered Materials Sector, Morristown, N.J. under the trademark VECTOMER 4010), a vinyl ether terminated aliphatic ester monomer (e.g., cyclohexane dimethanol monovinyl ether glutarate which can be purchased from Allied-Signal Inc. under the trademark VECTOMER 4020), a vinyl ether terminated aliphatic urethane oligomer (e.g., VECTOMER 2020 which can be purchased from Allied-Signal Inc.), and a vinyl ether terminated aromatic urethane oligomer (e.g., VECTOMER 2015 and VECTOMER 2010, both of which can be purchased from Allied-Signal Inc.

Blends of various cationically polymerizable resins are also contemplated in this invention. Examples of such blends include two or more weight average molecular weight distributions of resin-containing compounds, such as low molecular weight (below 200), intermediate molecular weight (about 200 to 10,000) and higher molecular weight (above about 10,000). Alternatively or additionally, the resin may contain a blend of resin-containing materials having different chemical natures, such as aliphatic and aromatic, or functionalities, such as polar and non-polar. Other cationically polymerizable polymers may additionally be incorporated, if desired.

If desired, the photopolymerizable composition can also contain a free-radically polymerizable material, including ethylenically unsaturated monomer, monomers or oligomers or polymers. Suitable materials contain at least one ethylenically unsaturated bond, and are capable of undergoing addition polymerization. Such free-radically polymerizable materials include mono-, di- or poly-acrylates and methacrylates such as methyl acrylate, methyl methacrylate, ethyl acrylate, isopropyl methacrylate, n-hexyl acrylate, stearyl acrylate, allyl acrylate, glycerol diacrylate, glycerol triacrylate, ethyleneglycol diacrylate, diethyleneglycol diacrylate, triethyleneglycol dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, bis[1-(2-acryloxy)]-p-ethoxyphenyldimethylmethane, bis[1-(3-acryloxy-2-hydroxy)]-p-propoxyphenyldimethylmethane, and trishydroxyethyl-isocyanurate trimethacrylate; the bisacrylates and bis-methacrylates of polyethylene glycols of molecular weight 200-500, copolymerizable mixtures of acrylated monomers such as those in U.S. Pat. No. 4,652,274, and acrylated oligomers such as those of U.S. Pat. No. 4,642,126; and vinyl compounds such as styrene, diallyl phthalate, divinyl succinate, divinyl adipate and divinylphthalate. Mixtures of two or more of these free radically polymerizable materials can be used if desired.

If desired, the polymerizable material(s) may contain both cationically polymerizable and free-radically polymerizable functionalities in a single molecule. These may be obtained, for example, by reacting a di- or poly-epoxide with one or more equivalents of an ethylenically unsaturated carboxylic acid. Examples of such materials include the reaction product of UVR-6105 (available from Union Carbide) or DER 332 (available from Dow Chemical Co.) with one equivalent of methacrylic acid. Commercially available materials having epoxy and free-radically polymerizable functionalities include the "Cyclomer" series, such as Cyclomer M100 or M101, available from Daicel Chemical, Japan.

The polymerizable material(s) can also contain hydroxyl and free-radically polymerizable functionalities in a single molecule. Examples of such materials include hydroxylalkylacrylates and hydroxyalkylmethacrylates such as hydroxyethylacrylate, hydroxyethylmethacrylate; glycerol mono- or di-acrylate and methacrylate; and the like.

The optional hydroxyl-containing material that may be used in the present invention can be any organic material having hydroxyl functionality of at least 1 or at least 2.

Preferably the hydroxyl-containing material contains two or more primary or secondary aliphatic hydroxyl groups (i.e., the hydroxyl group is bonded directly to a non-aromatic carbon atom). The hydroxyl groups can be terminally situated, or they can be pendent from a polymer or copolymer. The molecular weight of the hydroxyl-containing organic material can vary from very low (e.g., 32) to very high (e.g., one million or more). Suitable hydroxyl-containing materials can have low molecular weights, i.e. from about 32 to 200, intermediate molecular weight, i.e. from about 200 to 10,000, or high molecular weight, i.e. above about 10,000. As used herein, all molecular weights are weight average molecular weights.

The hydroxyl-containing material can optionally contain other functionalities that do not substantially interfere with cationic polymerization at room temperature. Thus, the hydroxyl-containing materials can be nonaromatic in nature or can contain aromatic functionality. The hydroxyl-containing material can optionally contain heteroatoms in the backbone of the molecule, such as nitrogen, oxygen, sulfur, and the like, provided that the ultimate hydroxyl-containing material does not substantially interfere with cationic polymerization at room temperature. The hydroxyl-containing material can, for example, be selected from naturally occurring or synthetically prepared cellulosic materials. Of course, the hydroxyl-containing material is also substantially free of groups that may be thermally or photolytically unstable; that is, the material will not decompose or liberate volatile components at temperatures below about 100° C. or in the presence of actinic light that may be encountered during the desired polymerization conditions for the photocopolymerizable composition.

Representative examples of suitable hydroxyl-containing materials having a hydroxyl functionality of 1 include alkanols, monoalkyl ethers of polyoxyalkyleneglycols, monoalkyl ethers of alkylene-glycols, and others known in the art.

Representative examples of useful monomeric polyhydroxy organic materials include alkylene glycols (e.g., 1,2-ethanediol; 1,3-propanediol; 1,4-butanediol; 1,6-hexanediol; 1,8-octanediol; 2-ethyl-1,6-hexanediol; bis(hydroxymethyl) cyclohexane; 1,18-dihydroxyoctadecane; 3-chloro-1,2-propanediol); polyhydroxyalkanes (e.g., glycerine, tri-methylolethane, pentaerythritol, sorbitol) and other polyhydroxy compounds such as N,N-bis(hydroxyethyl)benzamide; 2-butyne-1,4-diol; 4,4-bis(hydroxymethyl)diphenylsulfone; castor oil; and the like.

Representative examples of useful polymeric hydroxyl-containing materials include polyoxyethylene and polyoxypropylene glycols, and particularly the polyoxyethylene and polyoxypropylene glycol diols and triols having molecular weights from about 200 to about 10,000 corresponding to a hydroxy equivalent weight of 100 to 5000 for the diols or 70 to 3300 for triols; polytetramethylene ether glycols such as polytetrahydrofuran or "poly THF" of varying molecular weight; copolymers of hydroxypropyl and hydroxyethyl acrylates and methacrylates with other free radical-polymerizable monomers such as acrylate esters, vinyl halides, or styrene; copolymers containing pendent hydroxy groups formed by hydrolysis or partial hydrolysis of vinyl acetate copolymers, polyvinylacetal resins containing pendent hydroxyl groups; modified cellulose polymers such as hydroxyethylated and hydroxypropylated cellulose; hydroxy-terminated polyesters; hydroxy-terminated polylactones, and particularly the polycaprolactones; fluorinated polyoxyethylene or polyoxypropylene glycols; and hydroxy-terminated polyalkadienes.

Useful commercially available hydroxyl-containing materials include the "TERATHANE" series of polytetramethylene ether glycols such as "TERATHANE" 650, 1000, 2000 and 2900 (available from du Pont de Nemours, Wilmington, Del.), polytetrahydrofuran with an average molecular weight of 250 (available from Sigma-Aldrich, St. Louis, Mo.), the "PEP" series of polyoxyalkylene tetrols having secondary hydroxyl groups such as "PEP" 450, 550 and 650; "BUTVAR" series of polyvinylacetal resins such as "BUTVAR" B-72A, B-73, B-76, B-90 and B-98 (available from Monsanto Chemical Company, St. Louis, Mo.); and the "FORMVAR" series of resins such as 7/70, 12/85, 7/95S, 7/95E, 15/95S and 15/95E (available from Monsanto Chemical Company); the "TONE" series of polycaprolactone polyols such as "TONE" 0200, 0210, 0230, 0240, 0300 and 0301 (available from Union Carbide); "PARAPLEX U-148" aliphatic polyester diol (available from Rohm and Haas, Philadelphia, Pa.), the "MULTRON" R series of saturated polyester polyols such as "MULTRON" R-2, R-12A, R-16, R-18, R-38, R-68 and R-74 (available from Mobay Chemical Co.); "KLUCEL E" hydroxypropylated cellulose having an equivalent weight of approximately 100 (available from Hercules Inc.); "Alcohol Soluble Butyrate" cellulose acetate butyrate ester having a hydroxyl equivalent weight of approximately 400 (available from Eastman Kodak Co., Rochester, N.Y.); polyether polyols such as polypropylene glycol diol (e.g., "ARCOL PPG-425", "Arcol PPG-725", "ARCOL PPG-1025", "ARCOL PPG-2025", ARCOL PPG-3025", "ARCOL PPG-4025" from ARCO Chemical Co.); polypropylene glycol triol (e.g., "ARCOL LT-28", "ARCOL LHT-42", "ARCOL LHT 112", "ARCOL LHT 240", "ARCOL LG-56", "ARCOL LG-168", "ARCOL LG-650" from ARCO Chemical Co.); ethylene oxide capped polyoxypropylene triol or diol (e.g., "ARCOL 11-27", "ARCOL 11-34", "ARCOL E-351", "ARCOL E-452", "ARCOL E-785", "ARCOL E-786" from ARCO Chemical Co.); ethoxylated bis-phenol A; propylene oxide or ethylene oxide-based polyols (e.g., "VORANOL" polyether polyols from the Dow Chemical Co.).

The amount of hydroxyl-containing organic material optionally used in the compositions of the invention may vary over broad ranges, depending upon factors such as the compatibility of the hydroxyl-containing material with the resin, the equivalent weight and functionality of the hydroxyl-containing material, the physical properties desired in the final cured composition, the desired speed of photopolymerization, and the like.

Blends of various hydroxyl-containing materials are also contemplated in this invention. Examples of such blends include two or more molecular weight distributions of hydroxyl-containing compounds, such as low molecular weight (below 200), intermediate molecular weight (about 200 to 10,000) and higher molecular weight (above about 10,000). Alternatively or additionally, the hydroxyl-containing material can contain a blend of hydroxyl-containing materials having different chemical natures, such as aliphatic and aromatic, or functionalities, such as polar and non-polar. As an additional example, one may use mixtures of two or more poly-functional hydroxy materials or one or more mono-functional hydroxy materials with poly-functional hydroxy materials.

The cationically polymerizable resin, optional hydroxy-containing material(s), and optional free radically polymerizable material(s) are combined with a three-component or ternary photoinitiator system.

The inventive dental composition may comprise a filler matrix. The filler matrix can be comprised of one filler or a mixture of different fillers.

The nature of filler of the inventive composition is not particularly limited. The size of the filler particles should be such that a homogeneous mixture with the hardenable component(s) forming the resin matrix can be obtained.

Useful fillers include fumed silica, fillers based on fluoroaluminosilicate glasses, quartz, ground glasses, non-water-soluble fluorides such as $CaF_2$, silica gels such as silicic acid, in particular pyrogenic silicic acid and granulates thereof, cristobalite, calcium silicate, zirconium silicate, zeolites, including the molecular sieves, metal oxide powders, such as aluminium or zinc oxides or their mixed oxides, barium sulphate, yttrium fluoride, calcium carbonate.

The silica is usually dispersed within the resin matrix. The silica particles used in the dental compositions of the invention preferably have an average diameter of less than about 200 nm; more preferably, the particles are less than about 100 nm in average diameter. These measurements are preferably based on a TEM (transmission electron microscopy) method, whereby a population is analyzed to obtain an average particle diameter. A preferred method for measuring the particle diameter can be described is as follows:

Samples approximately 80 nm thick are placed on 200 mesh copper grids with carbon stabilized formvar substrates (SPI Supplies—a division of Structure Probe, Inc., West Chester, Pa.). A transmission electron micrograph (TEM) is taken, using JEOL 200CX (JEOL, Ltd. of Akishima, Japan and sold by JEOL USA, Inc.) at 200 Kv. A population size of about 50-100 particles can be measured and an average diameter is determined.

The average surface area of the silica particles is preferably greater than about 15 $m^2$/g more preferably greater than about 30 $m^2$/g.

Once dispersed in the resin, the silica particles are in a discrete (individual) and unassociated (i.e. non-agglomerated, non-aggregated) condition. "Agglomerated" as used herein, is descriptive of a weak association of particles usually held together by charge or polarity and can be broken down into smaller entities. "Aggregated," as used herein, is descriptive of a strong association of particles often bound together by, for example, residual chemicals treatment; further breakdown of the aggregates into smaller entities is very difficult to achieve.

The silica particles which can be used in the dental materials of the invention are preferably substantially spherical and substantially non-porous. Although the silica is preferably essentially pure, it may contain small amounts of stabilizing ion such as ammonium and alkaline metal ions.

Suitable fumed silicas include for example, products sold under the tradename AEROSIL series OX-50, -130, -150, and -200 available from Degussa AG, (Hanau, Germany), and CAB-O-SIL M5 available from Cabot Corp (Tuscola, Ill.).

Useful fluoroaluminosilicate glasses include silanol treated fluoroaluminosilicate glass fillers, as described in U.S. Pat. No. 5,332,429, the disclosure of which is expressly incorporated by reference herein. For example, a fluoride releasing glass may be added to the dental composition to provide the benefit of long-term release of fluoride in use, for example in the oral cavity.

Optionally, a heavy metal oxide can be included in the dental materials of the invention to provide a radiopaque dental material. It is preferred that the heavy metal oxide be present in an amount effective to impart radiopacity. As used herein, "radiopacity" describes the ability of a hardened dental material to be distinguished from tooth structure using standard dental X-ray equipment in the conventional manner. Radiopacity in a dental material is advantageous in certain instances where X-rays are used to diagnose a dental condition. For example, a radiopaque material would allow the detection of secondary caries that may have formed in the tooth tissue surrounding a filling. The desired degree of radiopacity can be varied, depending upon the particular application and the expectations of the practitioner evaluating the X-ray film.

Oxides of heavy metals having an atomic number greater than about 28 can be preferred. The heavy metal oxide should be chosen such that undesirable colors or shading are not imparted to the hardened resin in which it is dispersed. For example, iron and cobalt would not be favoured, as they impart dark and contrasting colors to the neutral tooth color of the dental material. More preferably, the heavy metal oxide is an oxide of metals having an atomic number greater than 30. Suitable metal oxides are the oxides of yttrium, strontium, barium, zirconium, hafnium, niobium, tantalum, tungsten, bismuth, molybdenum, tin, zinc, lanthanide elements (i.e. elements having atomic numbers ranging from 57 to 71, inclusive), cerium and combinations thereof. Most preferably, the oxides of heavy metals having an atomic number greater than 30, but less than 72 are optionally included in the materials of the invention. Particularly preferred radiopacifying metal oxides include lanthanum oxide, zinc oxide, tin oxide, zirconium oxide, yttrium oxide, ytterbium oxide, barium oxide, strontium oxide, cerium oxide, and combinations thereof. The heavy metal oxide particles may be aggregated. If so, it is preferred that the aggregated particles are less than about 200 nm, and more preferably are less than about 90 nm in average diameter.

In a preferred embodiment the filler matrix comprises a nano-sized filler including nano-sized silica.

Preferred nano-sized silicas are commercially available from Nalco Chemical Co. (Naperville, Ill.) under the product designation NALCO COLLOIDAL SILICAS. For example, preferred silica particles can be obtained from using NALCO products 1040, 1042, 1050, 1060, 2327 and 2329. In a preferred embodiment where the hardenable resin employs a cationic initiation system, the starting silica is preferably acidic (such as Nalco 1042).

Surface-treating the nano-sized silica particles before loading into the dental material can provide a stable dispersion in the resin. "Stable", as used herein, means a dental material in which the particles do not agglomerate after standing for a period of time, such as about 24 hours, under standard ambient conditions, e.g. room temperature (about 20 to about 22° C.), atmospheric pressure, and no extreme electromagnetic forces. Preferably, the surface-treatment stabilizes the nano-sized particles so that the particles will be well dispersed in the hardenable resin and results in a substantially homogeneous composition. Furthermore, it is preferred that the silica be modified over at least a portion of its surface with a surface treatment agent so that the stabilized particle can copolymerize or otherwise react with the hardenable resin during curing.

The silica particles can be treated with a resin-compatibilizing surface treatment agent. Particularly preferred surface treatment or surface modifying agents include silane treatment agents capable of polymerizing with a resin. Preferred silane treatment agent include γ-methacryloxylpropyltrimethoxysilane, available commercially under the trade designation A-174, available commercially from Witco OSi Specialties (Danbury, Conn.) and γ-glycidoxypropyltrimethoxy silane, a product available under the trade designation G6720, available from United Chemical Technologies (Bristol, Pa.).

Alternatively a combination of surface modifying agents can be useful, wherein at least one of the agents has a functional group co-polymerizable with a hardenable resin. For example, the polymerizing group can be ethylenically unsaturated or a cyclic function subject to ring opening polymerization. An ethylenically unsaturated polymerizing group can be, for example, an acrylate or methacrylate, or vinyl group. A cyclic functional group subject to ring opening polymerization generally contains a heteroatom such as oxygen, sulfur or nitrogen, and preferably is a 3-membered ring containing oxygen such as an epoxide. Other surface modifying agents which do not generally react with hardenable resins can be included to enhance dispersibility or rheological properties. Examples of silane of this type include, for example, alkyl or aryl polyethers, alkyl, hydroxy alkyl, hydroxy aryl, or amino alkyl functional silanes.

Upon surface treating the silica particles, they can then be combined with an appropriate hardenable resin to form a dental composition of the invention.

The filler matrix can comprise at least about 25 wt.-% or at least about 30 wt.-% or at least about 40 wt.-% or at least about 50 wt.-% of the whole composition.

The amount of filler to be used in the filler matrix usually depends on the purpose for which the composition should be used.

The filler matrix can comprise up to about 90 wt.-% or up to about 85 wt.-% or up to about 80 wt.-% of the whole composition.

Temporary crown and bridge materials (as an example for a dental composition) usually do not contain a high amount of fillers. With respect to these compositions, the filler content usually is in a range of about 30 to about 60 wt.-% with respect to the whole composition.

In dental filling materials (as another example for a dental composition), which typically contain a higher amount of fillers compared to temporary crown and bridge materials, the filler content is usually in a range of about 60 to about 90 wt.-% with respect to the whole composition.

Cationically polymerizable compositions of the invention can be prepared with refractive indices which approach or approximate the refractive indices of fillers such as quartz (refractive index 1.55), submicron silica (refractive index 1.46), and 5.5:1 mole ratio SiO:ZrO, non-vitreous microparticles (refractive index 1.54). In this way, the appearance of the dental material can, if desired, be made to closely approximate the appearance of natural dentition.

The compositions of the invention can also contain suitable adjuvants such as accelerators, inhibitors or retarders, absorbers, stabilizers, pigments, dyes, viscosity modifiers, surface tension depressants and wetting aids, antioxidants, and other ingredients well known to those skilled in the art.

The amounts and types of each ingredient in the composition should be adjusted to provide the desired physical and handling properties before and after polymerization. For example, the polymerization rate, polymerization stability, fluidity, compressive strength, tensile strength and durability of the dental material typically are adjusted in part by altering the types and amounts of polymerization initiator(s) and, if present, the loading and particle size distribution of filler(s). Such adjustments typically are carried out empirically based on experience with dental materials of the prior art.

Typical adjuvants include pigments, colorants and/or dyes. Examples include titanium dioxide or zinc sulphide (lithopones), red iron oxide 3395, Bayferrox 920 Z Yellow, Neazopon Blue 807 (copper phthalocyanine-based dye) or Helio Fast Yellow ER. These additives may be used for individual coloring of the dental compositions.

Further additives, which can be added, include stabilizers, especially free radical scavengers such as substituted and/or unsubstituted hydroxyaromatics (e.g. butylated hydroxytoluene (BHT), hydroquinone, hydroquinone monomethyl ether (MEHQ), 3,5-di-tert-butyl-4-hydroxyanisole (2,6-di-tert-butyl-4-ethoxyphenol), 2,6-di-tert-butyl-4-(dimethylamino) methylphenol or 2,5-di-tert-butyl hydroquinone, 2-(2'-hydroxy-5'-methylphenyl)-2H-benzotriazole, 2-(2'-hydroxy-5'-t-octylphenyl)-2H-benzotriazole, 2-hydroxy-4-methoxybenzophenone (UV-9), 2-(2'-hydroxy-4',6'-di-tert-pentylphenyl)-2H-benzotriazole, 2-hydroxy-4-n-octoxybenzophenone, 2-(2'-hydroxy-5'-methacryloxyethylphenyl)-2H-benzotriazole, phenothiazine, and HALS (hindered amine light stabilizers). Such adjuvants may optionally comprise reactive functionality so that they will be copolymerized with the resin.

There is no absolute need for these adjuvants to be present, so adjuvants might not be present at all. However, if they are present they are typically present in an amount of at least about 0.01 wt.-% or at least about 0.5 wt.-% or at least about 1 wt.-% with respect to the whole composition.

The adjuvants can be present in an amount up to about 25 wt.-% or up to about 20 wt.-% or up to about 15 wt.-% with respect to the whole composition.

The curable composition of the invention can be obtained by combining (including mixing and kneading) the individual components of the composition, preferably under "safe light" conditions.

Suitable inert solvents may be employed if desired when formulating this mixture. Any solvent may be used which does not react appreciably with the components of the inventive compositions. Examples of suitable solvents include acetone, dichloromethane, acetonitrile and lactones. A liquid material to be polymerized may be used as a solvent for another liquid or solid material to be polymerized. Solventless compositions can be prepared by simply dissolving the iodonium complex salt, sensitizer, and electron donor in the cationically polymerizable resin, with or without the use of mild heating to facilitate dissolution.

The individual components of the ternary photoinitiator system are provided in photopolymerizingly effective amounts (i.e., amounts effective to yield a photoinitiator system that can initiate photopolymerization of the cationically polymerizable resin or, more preferably, that can accelerate the rate of polymerization).

Typically, the visible light sensitizer can be present at about 0.03 to about 5 wt.-% based on the overall photopolymerizable composition, or from about 0.10 to about 2.0 wt.-%. The iodonium salt can be present at about 0.05 to about 10 wt.-%, or at about 0.1 to about 5 wt.-%, or about 0.5 to about 3 wt.-%, based on the overall composition. The electron donor compound can be present at about 0.005 to about 5 wt.-%, or about 0.01 to about 1 wt.-%.

Thus, the hardenable composition can comprise (with respect to the whole composition):
- the photoinitiator system in an amount of at least about 0.15 wt.-% or at least about 0.35 wt.-% or at least about 0.7 wt.-% or at least about 1.4 wt.-% or at least about 2.80 wt.-%,
- the cationically polymerizable resin in an amount of at least about 5 wt.-% or at least about 15 wt.-% or at least about 35 wt.-% or at least about 65 wt.-%,
- optionally hydroxyl group containing material(s) in an amount of utmost about 5 wt.-% or of utmost about 3 wt.-% or of utmost about 1 wt.-% and
- optionally filler(s) in an amount of utmost about 90 wt.-% or of utmost about 80 wt.-% or of utmost about 60 wt.-% or of utmost about 30 wt.-%,
- optionally adjuvants in an amount of utmost about 20 wt.-% or of utmost about 10 wt.-% or of utmost about 5 wt.-% or of utmost about 3 wt.-%.

The inventive dental composition is typically stored in a container until use. Depending on the initiator system chosen, various containers can be suitable.

If the dental composition is provided as a one-component system, it can be stored in a container having only one chamber such as a compule. The compule has typically a cylindrical housing with a front and a rear end and a nozzle. The rear end of the housing is usually sealed with a movable piston. Typically, the dental composition is dispensed out of the compule or container using an applier having a movable plunger (e.g. an application device having the shape of a caulk gun). Examples of suitable compules or containers are described in U.S. Pat. No. 5,624,260, EP 1 340 472 A1, US 2007/0172789 A1, U.S. Pat. No. 5,893,714 and U.S. Pat. No. 5,865,803, the content of which with regard to the description of compules or containers is herewith incorporated by reference.

Alternatively, if the dental composition is provided as a two-component system, it can be stored in a dual-chamber container or cartridge and is mixed before use.

Cartridges which can be used are described e.g. in US 2007/0090079 or U.S. Pat. No. 5,918,772, the disclosure of which is incorporated by reference. Cartridges which can be used are commercially available from SulzerMixpac AG (Switzerland).

Static mixing tips which can be used are described e.g. in US 2006/0187752 or in U.S. Pat. No. 5,944,419, the disclosure of which is incorporated by reference. Mixing tips which can be used are commercially available from SulzerMixpac AG (Switzerland).

The present invention provides a system for polymerizing cationically polymerizable resins in an acceptable time frame, e.g., less than about 120 seconds (s) or less than about 100 s or less than about 60 s, and to a sufficient depth using visible light source equipment already available in the dental office or electronics fabrication facilities.

The compositions of the invention are particularly well adapted for use as a wide variety of dental materials, which may be filled or unfilled. Such dental materials include direct aesthetic restorative materials (e.g., anterior and posterior restoratives), prostheses, adhesives and primers for oral hard tissues, sealants, veneers, cavity liners, orthodontic bracket adhesives for use with any type of bracket (such as metal, plastic and ceramic), crown and bridge cements, artificial crowns, artificial teeth, dentures, and the like. These dental materials are used in the mouth and are disposed adjacent to natural teeth. The phrase "disposed adjacent to" as used herein refers to the placing of a dental material in temporary or permanent bonding (e.g., adhesive) or touching (e.g., occlusal or proximal) contact with a natural tooth. The term "composite" as used herein in the context of a dental material refers to a filled dental material. The term "restorative" as used herein refers to a dental composite that is polymerized after it is disposed adjacent to a tooth. The term "prosthesis" as used herein refers to a composite that is shaped and polymerized for its final use (e.g., as a crown, bridge, veneer, inlay, onlay or the like) before it is disposed adjacent to a tooth. The term "sealant" as used herein refers to a lightly filled dental composite or to an unfilled dental material that is cured after it is disposed adjacent to a tooth.

When the dental material is applied to a tooth, the tooth can optionally be pre-treated with a primer such as dentin or enamel adhesive by methods known to those skilled in the art.

The invention is also directed to the use of the inventive photoinitiator system for the production of a dental composition or material, the process of using comprising the steps of:
a) placing the dental composition comprising the photoinitiator system in contact with a tooth,
b) hardening the composition.

In addition to use in dental applications, the useful combination of high cure speed, high cure depth, temperature insensitivity and low colour formation achievable with this invention in low-stress epoxy resins could find use in other applications.

These could include hardcoats for a variety of substrates including various metals, glasses, plastics, papers, wood and the like. Other potential applications include graphic arts imaging (including curable inks, silverless imaging layers, an imaging layer on a projection plate, an imaging layer on a laser plate), photoresists, solder masks, electronic coatings, photocurable adhesives (including orthodontics), non-dental photocurable composites (including automotive parts or repair), a hard coat layer on an optical lens, or a coating on an optical fibre.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. The above specification, examples and data provide a description of the manufacture and use of the compositions and methods of the invention. The invention is not limited to the embodiments disclosed herein. One skilled in the art will appreciate that many alternative embodiments of the invention can be made without departing from the spirit and scope of thereof.

EXAMPLES

Unless otherwise indicated, all parts and percentages are on a weight basis, all water is deionized water, and all molecular weights are weight average molecular weight. Moreover, unless otherwise indicated all Experiments were conducted at ambient conditions (23° C.; 1013 mbar).

TABLE 1

| | Abbreviations | |
|---|---|---|
| | | Description and Source of Material |
| a | Methylbis[2-(7-oxabicyclo-[4.1.0]hept-3-yl)ethyl]phenyl silane | Silorane resin; as described for "Monomer Composition 2" in U.S. patent application No. 2003/0035899 (Klettke et al.) |
| b | 1,3,5,7-Tetrakis(1,2-ethanediyl-3,4-epoxycyclo-hexyl)-1,3,5,7-tetramethyl-cyclotetra-siloxane | Silorane resin as described for "Monomer Composition 2" in U.S. patent application No. 2003/0035899 (Klettke et al) |
| c | CQ | Camphorquinone (Sigma-Aldrich) |
| d | Anthracene | 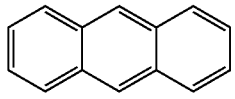<br>(Sigma-Aldrich) |
| e | EDMO | 2-Ethyl-9,10-dimethoxyanthracene (Sigma-Aldrich)<br>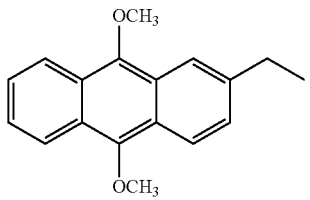 |

TABLE 1-continued
Abbreviations
Description and Source of Material
| | | |
|---|---|---|
| f | BP | Biphenylene 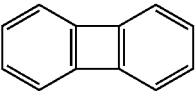 |
| g | DBBP | 2,6-Di-tert-butyl-biphenylene and 2,7-Di-tert-butyl-biphenyllene 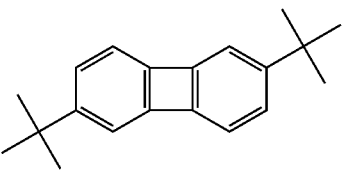 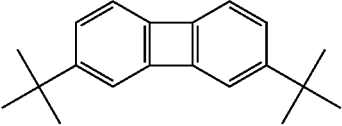 [SMILES: CC(C)(C)c1ccc2c(c1)-c1cc(C(C)(C)C)ccc1-2] |
| h | DMBP | 2,6-Dimethyl-biphenylene and 2,7-Dimethyl-biphenylene 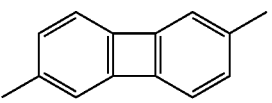 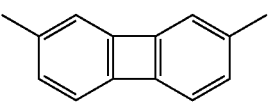 |
| i | TMBP | 2,3,6,7-Tetramethyl-biphenylene 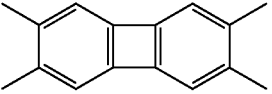 |
| j | DOBP | 2,6-Dimethoxy-biphenylene and 2,7-Dimethoxy-biphenylene 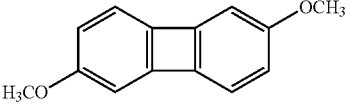 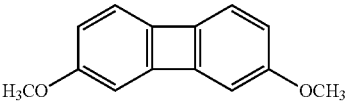 |
| k | BOBP | 2,3,6,7-Bis(methylendioxy)-biphenylene 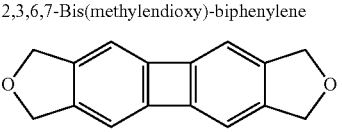 [SMILES: c1c2c(cc3c1-c1cc4c(cc1-3)COC4)COC2] |

TABLE 1-continued

Abbreviations

Description and Source of Material

| | | |
|---|---|---|
| l | OMBP | 1,2,3,4,5,6,7,8-Octamethylbiphenylene (Sigma-Aldrich) |
| m | Rhodia Silbione PI | (4-Cumyl)-(4-tolyl)iodonium Tetrakis(2,3,4,5,6-pentafluorophenyl)borate |
| n | Filler | Silane-treated quartz filler [prepared by silane treating quartz (Quarzwerke GmbH, Germany) with 3-glycidyloxypropyl-trimethoxysilane (ABCR GmbH, Karlsruhe, Germany) at a level of 5% by weight using standard silane-treatment procedures.] |
| o | Radiopacifier | Yttriumtrifluoride ($YF_3$) |
| p | pTHF 250 | Polytetrahydrofuran, mean molecular weight 250 (Sigma-Aldrich) |

Measurements

Depth of Cure (DOC)

DOC was evaluated according to ISO 4049 using either a metal mould or a Delrin™ mould and is given in mm.

Depth of Cure Test Method A

Depth of cure (i.e., cure depth) was analyzed according to ISO 4049 by packing a paste sample into a cylindrical metal curing mould (8 mm deep, 4 mm diameter) and curing the sample for 40 seconds with an ELIPAR™ Trilight Standard (800 mW/cm$^2$) (3M ESPE Company). The cured sample was removed from the mould and uncured paste was scraped off of the sample with a plastic applicator after less than about one minute of curing. Results were reported as the average of three replicates.

Depth of Cure Test Method B

Depth of cure (i.e., cure depth) was analyzed as described in the Depth of Cure Test Method A according to ISO 4049, except that the curing mould was a 12 mm deep Delrin™ mold.

Colour Formation

Colour formation was determined according to the following procedure according to CIE-Lab system. According to the CIE-Lab system the L* value is correlated with brightness, the a* value is correlated with the red colour and the b* value is correlated with the yellow colour.

A test sample paste was pressed into a 1.5 mm thick mould (15 mm diameter) and irradiated for 20 seconds (s) with a broad spectrum white light and then for 4*50 seconds with a 800 mW/cm$^2$ curing light (ELIPAR™ Trilight Standard, 3M ESPE Company) in five partially overlapping curing areas with respect to the light tip outlet diameter.

The resulting cured disk was analyzed on a Hunter Lab Scan 045 (Hunter Associates Laboratory, Reston Va.) against a white background. Results were reported as colour values on the L* a* b* scale. The b* value (the amount of yellow coloration) is a particularly important value to monitor for aesthetically pleasing anterior dental restorative applications. Low b* values (below about 20) allow compositions to be formulated that match the lightest shades on the Vita™ shade guide.

Fluorescence

The fluorescence was evaluated as follows:

The cured disks prepared as described in the Colour Formation were analyzed on a SPACTRAmax GEMINI XS (Molecular Devices, Sunnyvale Calif.). Using a 24 well plate the disks were irradiated with monochromatic radiation of 355 nm wavelength at room temperature. The corresponding fluorescence emission spectra were recorded using the SOFTmax PRO software program (version Enterprise 4.8, Molecular Devices) in the wavelength range of 370 nm to 650 nm in steps of 10 nm each in the presence of the disk containing the reference compound as internal relative standard. The Absolute Fluorescence Emission Intensity is given in Relative Fluorescence Units (RFU). The Fluorescence Emission Wavelengths of the corresponding Maximum Fluorescence Emissions were determined in nm within the recorded range of 370 nm to 650 nm.

General Procedure A:

All operations were performed under a protective atmosphere of dry nitrogen. The 1,2-dibromo-benzene derivative was dissolved in anhydrous THF. The resulting solution was cooled to about −80° C. At this temperature n-butyl lithium in n-hexane or cyclohexane or tert-butyl lithium in n-pentane was added slowly. After completion of the addition the solution was warmed to about −50° C. At this temperature anhydrous zinc dichloride was added and the resulting solution was stirred for about 15 min. The solution was cooled again to about −80° C. and anhydrous copper dichloride was added. The resulting suspension was stirred for about 120 min at about −80° C. and then allowed to warm to room temperature over night with stirring. Diethylether was added and the reaction mixture was extracted three times with water. The combined aqueous extracts were re-extracted three times with diethylether. The combined organic phases were dried with anhydrous sodium sulfate. After filtration the solvent was removed in vacuum and the remaining crude product was treated with ice cooled n-hexane or ice cooled diethylether.

After filtration the pure corresponding biphenylene derivative was isolated as a powder.

2,6/7-Di-tert-butylbiphenylene (DBBP)

Inventive Example 1

According to General Procedure A 510 g of 4-tert-butyl-1,2-dibromo-benzene and 1.05 kg of a solution of n-butyl lithium in cyclohexane (3.02 mmol of n-butyl lithium per 1 g of solution) were reacted in 20.0 l of anhydrous THF. After additions of 257 g of anhydrous zinc dichloride and 691 g of anhydrous copper dichloride and the standard workup procedure (treatment with ice cooled diethylether) finally 50.2 g (22.2%, m.p. 253° C.) of pure DBBP were isolated as colorless powder showing no fluorescence.

2,6/7-Dimethylbiphenylene (DMBP)

Inventive Example 2

According to General Procedure A 5.10 g of 4-methyl-1, 2-dibromo-benzene and 14.5 ml of a 2.50 M solution of n-butyl lithium in n-hexane are reacted in 300 ml of anhydrous THF. After additions of 3.00 g of anhydrous zinc dichloride and 8.10 g of anhydrous copper dichloride and following the workup procedure described above 306 mg (17.0%) of pure DMBP were isolated as yellowish powder showing no fluorescence.

2,3,6,7-Tetramethylbiphenylene (TMBP)

Inventive Example 3

According to General Procedure A 4.64 g of 4,5-dimethyl-1,2-dibromo-benzene and 9.10 g of a 2.50 M solution of n-butyl lithium in n-hexane were reacted in 300 ml of anhydrous THF. After additions of 2.56 g of anhydrous zinc dichloride and 6.88 g of anhydrous copper dichloride and following the workup procedure described above 388 mg (21.9%) of TMBP containing traces of the by-product 2,3,6, 7,10,11-hexamethyl-triphenylene were isolated as yellowish powder showing no fluorescence. Pure TMBP can be isolated via fractionated crystallization from cold diethylether.

Biphenylene (BP)

Comparative Example 3

According to General Procedure A 7.90 g of 1,2-dibromo-benzene and 44.5 ml of a 1.50 M solution of tert-butyl lithium in n-pentane were reacted in 500 ml of anhydrous THF. After additions of 5.00 g of anhydrous zinc dichloride and 13.5 g of anhydrous copper dichloride and following the workup procedure described above 865 mg (17.0%) of BP were isolated as colourless powder showing no fluorescence.

2,6/7-Dimethoxybiphenylene (DOBP)

Comparative Example 4

According to General Procedure A 5.00 g of 4-methoxy-1,2-dibromo-benzene and 11.5 g of a solution of n-butyl lithium in cyclohexane (3.03 mmol of n-butyl lithium per 1 g of solution) were reacted in 200 ml of anhydrous THF. After additions of 2.82 g of anhydrous zinc dichloride and 7.58 g of anhydrous copper dichloride and following the workup procedure described above 100 mg (4.82%) of DOBP were isolated as yellow powder after additional flash column chromatography (silica gel, 95:5=n-hexane:ethylacetate).

2,3,6,7-Bis(methylenedioxy)biphenylene (BOBP)

Comparative Example 5

According to General Procedure A 5.10 g of 4,5-methenedioxy-1,2-dibromo-benzene and 9.53 g of a 2.50 M solution of n-butyl lithium in n-hexane were reacted in 300 ml of anhydrous THF. After additions of 2.68 g of anhydrous zinc dichloride and 7.20 g of anhydrous copper dichloride and following the workup procedure described above 29.6 mg (1.39%) of BOBP were isolated as yellow powder after additional flash column chromatography (silica gel, 85:15=n-hexane: ethylacetate).

General Procedure B

With magnetic stirring and under the exclusion of light the initiator system components were dissolved within the monomers at temperatures not above 50° C. (depending on the intrinsic viscosity of the used monomers). The obtained dental composition was then light cured using a 800 mW halogen curing light (3M ESPE Elipar™ Trilight) and tested according to the corresponding measurements listed above.

TABLE 2

Cationically Curing Compositions Containing Anthracene Type and Biphenylene Type Initiator System Components

| | Cationically Curing Compositions[1] | | | | | | | | | |
|---|---|---|---|---|---|---|---|---|---|---|
| | A[2] | B[3] | C[4] | D[4] | E[5] | F[5] | G[5] | H[4] | I[4] | J[4] |
| a | 11.1 | 11.1 | 11.4 | 11.4 | 11.4 | 11.4 | 11.4 | 11.4 | 11.4 | 12.7 |
| b | 11.1 | 11.1 | 11.3 | 11.3 | 11.3 | 11.3 | 11.3 | 11.3 | 11.3 | 12.6 |
| c | 0.12 | 0.12 | 0.07 | 0.07 | 0.07 | 0.07 | 0.07 | 0.07 | 0.07 | 0.14 |
| d | 0.02 | | | | | | | | | |
| e | 0.01 | | | 0.02 | | | | | | |
| f | | | | | | 0.01 | | | | |
| g | | 0.02 | | | | | 0.02 | | | |
| h | | | | | | | | 0.01 | | |
| i | | | | | | | | | 0.01 | |
| j | | | | | | | | | | 0.02 |
| k | | | | | | | | | | 0.02 |
| l | | | | | | | | | | 0.03 |
| m | 0.71 | 0.72 | 0.35 | 0.35 | 0.35 | 0.35 | 0.35 | 0.35 | 0.35 | 0.81 |
| n | 64.7 | 64.7 | 65.0 | 65.0 | 65.0 | 65.0 | 65.0 | 65.0 | 65.0 | 61.0 |
| o | 11.5 | 11.5 | 11.5 | 11.5 | 11.5 | 11.5 | 11.5 | 11.5 | 11.5 | 11.9 |
| p | 0.71 | 0.72 | 0.35 | 0.35 | 0.35 | 0.35 | 0.35 | 0.35 | 0.35 | 0.81 |
| CS[6] | 329 ± 24.0 | 329 ± 21.0 | n.a. | n.a. | n.a. | n.a. | n.a. | n.a. | n.a. | 332 ± 28.0 |
| FS[7] | 126 ± 12.0 | 119 ± 5.00 | n.a. | n.a. | n.a. | n.a. | n.a. | n.a. | n.a. | 111 ± 10.0 |
| E-M.[8] | 10.1 ± 0.30 | 9.70 ± 0.40 | n.a. | n.a. | n.a. | n.a. | n.a. | n.a. | n.a. | 8.90 ± 0.50 |
| DOC[9] | 2.30 | 2.28 | 2.37 | 1.99 | 2.36 | 2.31 | 2.18 | 2.24 | 0.77 | 2.20 |
| DOC[10] | 3.97 | 3.96 | 3.87 | 3.27 | 3.60 | 3.74 | 3.50 | 3.69 | 1.01 | 3.80 |
| L*[11] | 75.8 | 79.3 | 76.6 | 79.0 | 78.9 | 76.7 | 76.6 | 64.6 | 64.1 | 61.0 |

TABLE 2-continued

Cationically Curing Compositions Containing Anthracene Type and Biphenylene Type Initiator System Components

| | Cationically Curing Compositions[1] | | | | | | | | | |
|---|---|---|---|---|---|---|---|---|---|---|
| | A[2] | B[3] | C[4] | D[4] | E[5] | F[5] | G[5] | H[4] | I[4] | J[4] |
| a*[12] | −4.30 | −1.40 | −5.00 | −1.90 | −2.00 | −1.30 | −1.30 | −0.30 | 4.30 | −1.00 |
| b*[13] | 16.4 | 9.80 | 14.7 | 10.7 | 8.20 | 11.5 | 11.6 | 31.6 | 33.3 | 24.0 |
| ACTA[14] | 1.80 ± 0.19 | 1.80 ± 0.19 | n.a. | n.a. | n.a. | n.a. | n.a. | n.a. | n.a. | n.a. |
| Watts[15] | 0.82 ± 0.03 | 0.86 ± 0.02 | n.a. | n.a. | n.a. | n.a. | n.a. | n.a. | n.a. | n.a. |
| $\lambda_{max, Em.}$[16] | 430 | 420 | 450 | 420 | 420 | 420 | 400 | 440 | 420 | 420 |
| Int.$_{Em.}$[17] | 24.0 | 7.17 | 100 | 8.40 | 5.74 | 8.00 | 36.5 | 6.56 | 34.8 | 1.64 |

[1]Amounts of ingredients are given in %-weight.
[2]kneaded paste, comparative example
[3]kneaded paste, inventive example
[4]speed mixed paste, comparative example
[5]speed mixed paste, inventive example
[6]Compressive Strength in MPa, cubic specimen, dimensions 3 mm × 3 mm × 5 mm
[7]Flexural Strength in MPa according to ISO 4049
[8]E-Modulus in GPa according to ISO 4049
[9]Depth of cure given in mm, metal mold, according to ISO 4049
[10]Depth of cure given in mm, Delrin ™ mold, according to ISO 4049
[11]L* value (i.e. brightness) according to CIE-Lab system
[12]a* value (i.e. red color) according to CIE-Lab system
[13]b* value (i.e. yellow color) according to CIE-Lab system
[14]Two Body Wear Resistance according to ACTA relative to 3M ESPE Filtek ™ Z250
[15]Bonded Disk Shrinkage-Strain in % according to the Watts protocol.
[16]Fluorescence Emission Wavelength of the Maximum Fluorescence Emission given in nm.
[17]Relative Fluorescence Emission Intensity at the Maximum Fluorescence Emission Wavelength given in rel.-% compared to the fluorescence emission intensity of the reference compound EDMO showing an Absolute Fluorescence Emission Intensity of 48800 RFU (Relative Fluorescence Units) at its Maximum Fluorescence Emission Wavelength of 450 nm.

As can be seen from Table 2, hardened compositions containing electron donors comprising biphenylene structures according to the invention show improved properties e.g. with respect to fluorescence, colour (especially b* value) and depth of cure in a metal mold compared to hardened compositions containing electron donors comprising either anthracene derivatives or biphenylene structures with a huge number of substituents attached onto the biphenylene structure.

The invention claimed is:

1. An initiator system comprising:
   (a) an iodonium salt;
   (b) a light sensitizer; and
   (c) an electron donor compound comprising a biphenylene structure, the biphenylene structure comprising at least 1 but not more than 4 alkyl substituents directly attached onto the biphenylene structure,
   wherein the electron donor compound is a biphenylene derivative having the following structure:

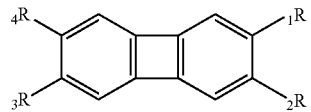

wherein each of $R_1$ to $R_4$ is independently selected from H or C1 to C5 allyl groups.

2. The initiator system according to claim 1, wherein the electron donor compound is characterized by at least one of the following features:
   soluble in a hardenable composition,
   substantially non-light absorbing at the wavelength at which the visible light sensitizer displays maximum light absorption,
   having a $pk_b$ greater than 8,
   oxidation potential less than about 1.35 volts when measured using a saturated calomel electrode.

3. The initiator system according to claim 1, wherein the electron donor compound is selected from the group consisting of

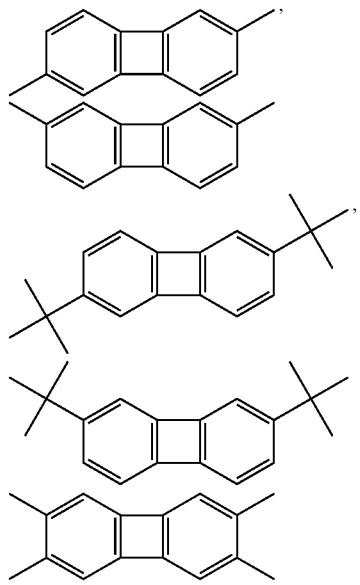

and combinations thereof.

4. The initiator system according to claim 1, wherein the iodonium salt is selected from the group consisting of diaryliodonium hexafluorophosphate, diaryl-iodonium hexafluoroantimonate, diaryliodonium tetrakis(pentafluorophenyl)borate, 4-octyloxyphenyl phenyliodonium hexafluoroantimonate, 4-(2-hydroxy-tetradecyloxyphenyl) phenyliodonium hexafluoroantimonate, 4-(1-methylethyl) phenyl 4-methylphenyliodonium tetrakis(pentafluorophenyl)borate, and combinations thereof.

5. The initiator system according to claim 1, wherein the light sensitizer is selected from the group consisting of ketones, coumarin dyes, xanthene dyes, fluorone dyes, fluorescein dyes, aminoketone dyes, p-substituted aminostyryl ketone compounds, and combinations thereof.

6. A hardenable composition comprising:
(a) a cationically polymerizable resin; and
(b) the initiator system described in claim 1.

7. The hardenable composition according to claim 6, wherein the cationically polymerizable resin is selected from the group consisting of epoxy, oxetane, vinyl ether, spiro-orthocarbonate resins, and combinations thereof.

8. The hardenable composition according to claim 7, wherein the cationically polymerizable resin comprises a silicon-containing epoxy resin.

9. The hardenable composition according to claim 6 further comprising at least one or more of the following components:
a free-radically polymerizable resin,
a hydroxyl-containing material,
a filler,
adjuvant(s),
and combinations thereof.

10. A method for curing a hardenable composition comprising the steps of:
providing a polymerizable composition as described in claim 6, and
exposing the polymerizable composition to a light source having a wavelength and intensity to which the initiator system being present in the polymerizable composition is reactive.

11. The method of claim 10, wherein said composition is irradiated with light for a period of time less than about 120 seconds.

12. An item comprising the hardenable composition according to claim 6, wherein the item is chosen form a photopolymerizable adhesive, a curable ink imaging layer, a silverless imaging layer, an imaging layer on a projection plate, an imaging layer on a laser plate, and a dental material.

13. An item comprising the hardenable composition according to claim 6, wherein the item is chosen from artificial crowns, anterior or posterior fillings, casting materials, cavity liners, cements, coating compositions, mill blanks, orthodontic devices, restoratives, prostheses or sealants, dental adhesives and dental composites.

14. A process for producing an electron donor compound comprising a biphenylene structure as described in claim 1, the biphenylene structure comprising at least 1 but not more than 4 alkyl substitutents, the process comprising the step of reacting a halogen-substituted benzene derivative with an organo Li reagent and subsequently with zinc chloride and copper chloride.

15. The process of claim 14, wherein the electron donor compound is characterized by at least one of the following features:
soluble in a hardenable composition,
substantially non-light absorbing at the wavelength at which the visible light sensitizer displays maximum light absorption,
a $pk_b$ greater than 8, and
oxidation potential less than about 1.35 volts when measured using a saturated calomel electrode.

16. The process of claim 14, wherein the electron donor compound is a biphenylene derivative having the following structure:

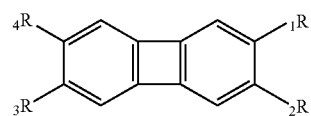

wherein each of $R_1$ to $R_4$ is independently selected from H, or C1 to C5 alkyl groups,
wherein the $R_1$ to $R_4$ may also cooperate to form a cycloalkyl ring.

17. The process of claim 14, wherein the electron donor compound is a biphenylene derivative selected from the group consisting of

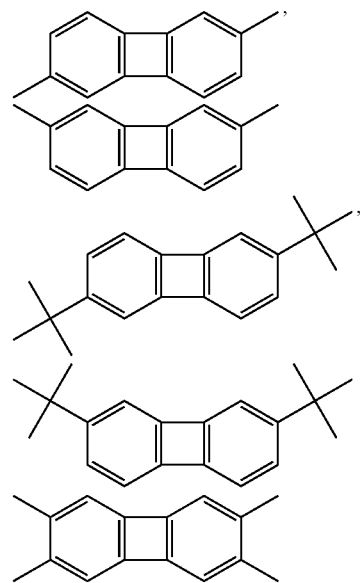

and combinations thereof.

18. The process of claim 14, wherein the process is carried out as a one-pot synthesis.

19. The hardenable composition of claim 9, wherein the composition has a depth of cure of at least 2.10 mm, if measured in a metal mould according to ISO 4049.

* * * * *

UNITED STATES PATENT AND TRADEMARK OFFICE
CERTIFICATE OF CORRECTION

PATENT NO. : 8,436,067 B2  
APPLICATION NO. : 12/996894  
DATED : May 7, 2013  
INVENTOR(S) : Thalacker et al.

Page 1 of 2

It is certified that error appears in the above-identified patent and that said Letters Patent is hereby corrected as shown below:

Title Page Col. 2 Item [56]
Line 1           Delete "Diarylidonium" and insert -- Diaryliodonium --, therefor.
Line 5           Delete "Meterials" and insert -- Materials --, therefor.
Line 6           Delete "Hydroxypropl" and insert -- Hydroxypropyl --, therefor.
Line 20          Delete "Alykl" and insert -- Alkyl --, therefor.
Line 28          Delete "Tehcniques" and insert -- Techniques --, therefor.

In the Specifications

Column 2
Line 21          Below "comprising:" insert -- (a) a cationically polymerizable resin; and --.

Column 3
Line 6           Delete "i.a." and insert -- i.e. --, therefor.

Column 8
Line 65          Delete "propy," and insert -- propyl, --, therefor.

Column 9
Line 55          Delete "hexane" and insert -- hexane. --, therefor.

Column 19
Lines 18-19      Delete "(lithopones)," and insert -- (lithophones), --, therefor.
Lines 19-20      Delete "Neazopon" and insert -- Neozapon --, therefor.

Column 25
Line 67          Delete "SPACTRA" and insert -- SPECTRA --, therefor.

Signed and Sealed this
Third Day of September, 2013

Teresa Stanek Rea
*Acting Director of the United States Patent and Trademark Office*

CERTIFICATE OF CORRECTION (continued)
U.S. Pat. No. 8,436,067 B2

Column 28
Lines 25-26          Delete "methenedioxy" and insert -- methylenedioxy --, therefor.

In the Claims

Column 29
Line 57              In Claim 1, delete "allyl" and insert -- alkyl --, therefor.

Column 31
Line 48              In Claim 14, delete "substitutents," and insert -- substituents, --, therefor.